United States Patent
Suzuki et al.

(10) Patent No.: US 10,654,890 B2
(45) Date of Patent: May 19, 2020

(54) CYCLIC PEPTIDE DERIVATIVE, METHOD FOR PREPARING SAME AND COMPOSITION THEREOF

(71) Applicants: NATIONAL UNIVERSITY CORPORATION, IWATE UNIVERSITY, Iwate (JP); OSAKA CITY UNIVERSITY, Osaka (JP); IWATE MEDICAL UNIVERSITY EDUCATIONAL FOUNDATION, Iwate (JP); LOTTE CO., LTD., Tokyo (JP)

(72) Inventors: Koichi Suzuki, Iwate (JP); Shinichi Ishiguro, Iwate (JP); Mayumi Karimazawa, Iwate (JP); Makiko Ebata, Iwate (JP); Piyamas Sillapakong, Iwate (JP); Takashi Hiraga, Iwate (JP); Masaaki Tsushima, Iwate (JP); Tetsuro Shinada, Osaka (JP); Eiji Nishimura, Osaka (JP); Yasuo Terayama, Iwate (JP); Hideyuki Yasuda, Saitama (JP)

(73) Assignee: BIOCOCOON LABORATORIES, INC., Iwate (JP)

( * ) Notice: Subject to any disclaimer, the term of this patent is extended or adjusted under 35 U.S.C. 154(b) by 0 days.

(21) Appl. No.: 16/144,266

(22) Filed: Sep. 27, 2018

(65) Prior Publication Data

US 2019/0085027 A1    Mar. 21, 2019

Related U.S. Application Data

(63) Continuation of application No. 15/512,619, filed as application No. PCT/JP2015/076797 on Sep. 18, 2015, now abandoned.

(30) Foreign Application Priority Data

Sep. 24, 2014 (JP) .................. 2014-194509

(51) Int. Cl.
| | | |
|---|---|---|
| C07K 5/12 | (2006.01) | |
| A61K 38/00 | (2006.01) | |
| C07K 5/107 | (2006.01) | |
| A61K 36/062 | (2006.01) | |

(52) U.S. Cl.
CPC ............ *C07K 5/126* (2013.01); *A61K 36/062* (2013.01); *A61K 38/00* (2013.01); *C07K 5/1016* (2013.01)

(58) Field of Classification Search
None
See application file for complete search history.

(56) References Cited

FOREIGN PATENT DOCUMENTS

| | | |
|---|---|---|
| JP | 2003-252876 | 9/2003 |
| JP | 2012-56867 | 3/2012 |
| JP | 2013-184923 | 9/2013 |

OTHER PUBLICATIONS

International Search Report dated Nov. 24, 2015 in International Application No. PCT/JP2015/076797.
Masaaki Tsushima et al., "Hot-water extract of *Paecilomyces tenuipes* from the silkworm pupae improves D-galactose-induced brain aging in mice", Journal of Insect Biotechnology and Sericology 79, 45-51 (2010).
International Preliminary Report on Patentability dated Nov. 24, 2015 in International Application No. PCT/JP2015/076797.

*Primary Examiner* — Adam Weidner
(74) *Attorney, Agent, or Firm* — Wenderoth, Lind & Ponack, L.L.P.

(57) ABSTRACT

Provided is a cyclic peptide derivative which is derived from *Paecilomyces tenuipes* having an astrocyte proliferative activity, or a salt thereof.

3 Claims, 16 Drawing Sheets
Specification includes a Sequence Listing.

CYCLIC PEPTIDE DERIVATIVE, METHOD FOR PREPARING SAME AND COMPOSITION THEREOF

TECHNICAL FIELD

The present invention relates to a cyclic peptide derivative, a method for preparing the same, and a composition thereof.

BACKGROUND ART

Insects, which are invertebrates have metabolism pathways or immune systems that are different from those of a vertebrate, and they exhibit resistance to pathogens or viruses based on strong natural immunity caused by various physiological substances synthesized in a living organism. Furthermore, by their ecology, insects also form a specific relationship with an external system, for example, other living organisms, pathogens, viruses, or the like. For such reasons, studies are under progress in recent years regarding the physiologically active substances that are derived from the insects or their ecology, and a large number of compounds having novel structure which have not been known before are being found.

As one background of the above, the inventors of the present invention have continuously performed a study on a pharmaceutical effect of plant worms and the like until now.

With regard to the classification and name of the plant worms, the phylogenetic relationship has been discussed and naming has been made all together while the morphology has been conventionally considered as a main aspect and expression of mating performance, ecology, pathogenic property, chemical classification, or the like is used as an indicator. Currently, based on molecular phylogenetic classification which uses a genotype as an indicator, a new classifying system is being constructed and established by determining again the phylogenetic relationship between *Cordyceps* genus and Clavicipitaceae family and also by considering the morphological characteristics. Accordingly, in the explanations that are given below, the Japanese name of the plant worms based on the descriptions of An Illustrated Guide to Ecology of Japanese *Cordyceps* (2014, published by SEIBUNDO SHINKOSHA) is described, and for those described for the first time, both the conventional name of species and the name of the species based on new classification are given in parentheses.

*Cordyceps* is one of the insect pathogen fungi sticking on an insect, and according to the interpretation in narrow sense, it indicates *Cordyceps sinennsis* (also referred to as *Cordyceps sinennsis* or *Ophiocordyceps sinennsis*) which lives in a high mountain area at 3,000 to 4,000 meters altitude in Nepal or Bhutan as well as Tibet Autonomous Region, Quinghai Province, Sichuan Province, Guizhou Province, Gansu Province, and Yunnan Province of China and it has, as a host, Endoclyta excrescens Butler belonging to Insecta, Lepidoptera, Hepialoidea, or Hepialidiae. There are various types of the host insect in a broad range in which Hemiptera, Lepidoptera, Coleoptera, Hymenoptera, Orthoptera, Odonata, and Diptera are included.

Incidentally, according to the interpretation in broad sense, the entire parasitic fungi living on adults or larvae of those insects are also referred to as the plat worms.

In addition, there is only little scientific knowledge available regarding the plant worm as a material for oriental medicine or a material for health supplementary food. Nevertheless, as an exemplary study on the physiological activity of the plant worms until now, *Cordyceps sinennsis* and a product thereof are widely used as a nutritional supplement which is effective for preventing diabetes, a cardiovascular disease, cancer, or a metabolism disease, or delaying the progress of those diseases (Non Patent Literature 1). Other than that, there are reports showing an anti-oxidation activity (Non Patent Literature 2), an immune-modulating activity (Non Patent Literature 3), an in vivo activity of lowering insulin resistance and enhancing insulins secretion in vivo (Non Patent Literature 4) by a water extraction of SANAGI-TAKE (*Cordyceps militaris*), an anti-hyperlipidemic effect (Non Patent Literature 5), an anti-cancer activity (Non Patent Literature 6), and an anti-inflammatory activity (Non Patent Literature 7) of a hot water extraction of *Cordyceps sinennsis*, which is *Cordyceps* found in Tibet. Furthermore, also according to a very recent report, it is shown that a physiologically active substance like cordycepin isolated from *Cordyceps sinennsis* has a novel physiological activity which has not been reported before (Non Patent Literatures 8 to 10). According to over-collecting due to a rapidly increasing demand based on such high popularity of *Cordyceps*, *Cordyceps sinennsis* from Tibet becomes highly expensive and is difficult to obtain.

Furthermore, since *Paecilomyces tenuipes* (also referred to as *Isaria japonica* Yasuda) as one type of the plant worms according to the interpretation in broad sense belongs to *Cordyceps* sp. of *Cordyceps* family of Ascomycetes and it is a parasitic fungus found on larvae or pupae of silkworm (*Bombyx mori*, and will be described as *B. mori* hereinbelow), artificial culture of *Cordyceps* based on combination with pupae of *B. mori* are recently commercialized in Japan. However, many commercially available products of the plant worms of *Cordyceps* sp., genus *Paecilomyces* and genus *Isaria* are mostly produced based on mycelial culture of asexual species, and also the research reports regarding the pharmaceutical effect of *Paecilomyces tenuipes* are significantly fewer than those regarding *Cordyceps sinennsis*.

As a physiologically active component of *Paecilomyces tenuipes* that is known until now, there is spirotenuipesine A and B which are obtained by drying and preparing in powder form a fruiting body of *Paecilomyces tenuipes* which has been cultured in a medium added with cereals, cereals or yeast or an extract thereof followed by extraction with 70% methanol and distribution with ethyl acetate and water, performing distribution of an aqueous phase with n-butanol and water, and treating an n-butanol phase with silica gel chromatography followed by elution with ethyl acetate (Patent Literature 1). Also known is cyclic hexadepsipetide Beauvericin which is isolated from an ethyl acetate extract of a mixture powder of a host (i.e., *B. mori* pupa) and a fruiting body and has an effect of inhibiting proliferation of rat cancer cells (Non Patent Literature 11), and hanasanagin (3,4-diguanidinobutanoyl-DOPA) which is obtained by using a fruiting body isolated from a host (i.e., *B. mori* pupa) as a raw material and performing the processes of 60% ethanol extraction, 5% methanol extraction, and hot water extraction, and has an activity of scavenging free radicals (DPPH) or an activity of scavenging superoxide anions (Non Patent Literatures 12 and 13).

Furthermore, the inventors of the present invention found that, while conducting a study on *Paecilomyces tenuipes* that is easier to obtain than *Cordyceps sinennsis* and thus is excellent in terms of cost and stable supply, an extraction fraction derived from powder of *Paecilomyces tenuipes* has an effect of improving the cerebral function of a mammal or has an activity of strongly promoting the proliferation of an astrocyte (Patent Literatures 2 and 3). Accordingly, inventors of the present invention continuously conducted additional intensive studies on the relationship between the astrocyte proliferative activity and *Paecilomyces tenuipes*.

An astrocyte (i.e., star-like glial cell) as one kind of glial cells makes up about a half of the entire cells in brain. From the viewpoint that the information processing function is carried out by a neuronal cell, it has been conventionally considered that the astrocyte present near neuronal cell has a function of supporting and protecting a neuronal cell, and supplying nutrients to the cell.

Incidentally, it has been demonstrated that the astrocyte itself participates in the cellular information processing because now there are reports suggesting that the astrocyte is a supplementary system for indirect forming of a neural network having an activity of forming a neural network (Non Patent Literatures 14 to 17) and an activity of regulating a transmitter concentration (Non Patent Literatures 18 and 19), and also it is capable of having an input from a neuronal cell and subsequent calcium propagation between astrocytes (Non Patent Literatures 20 to 22) and having an output to a neuronal cell including a synapse vesicular vesicle (Non Patent Literatures 23 and 24).

Furthermore, a study on the role of an astrocyte in forming of memory is also now carried out, and a higher brain function like memory is considered to be controlled by an interaction between a neuron and an astrocyte. For example, it is reported that the number of astrocyte increases in a hippocampus after forming of memory (Non Patent Literature 25) and forming of memory is inhibited if the function of an astrocyte is suppressed (Non Patent Literature 26).

Furthermore, as an abnormality in terms of anatomy of cerebral nerves which is commonly shown in a mental disease like an integration dysfunction syndrome, bipolar disorder, and depression, an enlargement of brain ventricle, and shrinkage of hippocampus and cerebral cortex size are seen at macro level. At micro level, shrinkage of a size of neuronal cell body, a decrease in density of dendritic spine, shortening of dendrite length, and a decrease in synapse-related proteins are known. They are considered to be a direct abnormality of a neuronal cell. However, it is reported recently that a decrease in the number of astrocyte is also commonly observed, and the possibility of having an indirect abnormality in neuronal cell state which is based on a decrease in the number of astrocyte is also determined (Non Patent Literature 27).

SUMMARY OF INVENTION

Technical Problem

However, even after the above Patent Literatures 2 and 3, the compound of which physiological function receives attention as a main body of exhibiting the effect of improving the cerebral function of a mammal or the activity of proliferating an astrocyte has still not been isolated or identified from *Paecilomyces tenuipes*.

The present invention is devised under the circumstances described above, and object of the invention is to provide a novel compound having an astrocyte proliferative activity, a method for preparing it, and a composition thereof.

Solution to Problem

The inventors of the present invention conducted intensive studies to solve the problems described above. Accordingly, as a result of purification based on two phase distribution, flash column chromatography, and reverse phase HPLC of a hot water extract of dry powder of *Paecilomyces tenuipes*, the inventors succeeded in isolation and purification of a novel cyclic peptide derivative. Accordingly, in addition to characterization of a chemical structure of the derivative, it was also found that the compound has a significant proliferative activity for an astrocyte derived from a neonatal mouse which has been subjected to primary culture and subculture, and the present invention has been completed based on those findings.

Namely, the novel compound of the present invention is characterized in that it is a cyclic peptide derivative that is represented by the following general formula (1).

[Chemical Formula 1]

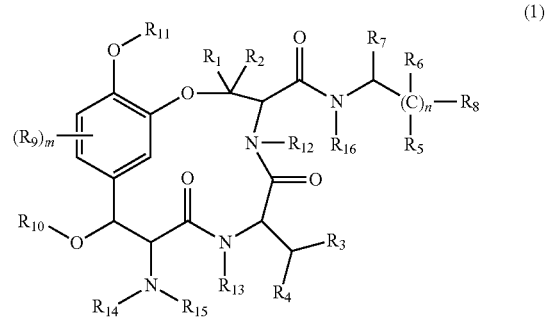

(1)

(in the formula, m is 0 to 3, n≥1, $R_1$ to $R_6$ are a hydrogen atom or a hydrocarbon group, $R_7$ and $R_8$ are a carboxyl group or a salt thereof, or an alkoxycarbonyl group, $R_9$ is a hydrocarbon group, a hydroxyl group, an alkoxy group, or an alkylcarbonyloxy group, $R_{10}$ and $R_{11}$ are a hydrogen atom, a hydrocarbon group, or an alkylcarbonyloxy group, and $R_{12}$ to $R_{16}$ are a hydrogen atom or a hydrocarbon group).

As the cyclic peptide derivative described above, it is preferable that, in the general formula (1), $R_1$, $R_2$, $R_3$, and $R_4$ are an alkyl group, n=2 to 4, $R_5$ and $R_6$ are a hydrogen atom, $R_7$ are $R_8$ a carboxyl group, and the like.

In a method for preparing a cyclic peptide derivative of the present invention, a case in which the cyclic peptide derivative is collected from *Paecilomyces tenuipes* is preferably considered.

Furthermore, a case in which *Paecilomyces tenuipes* are artificially cultured by using pupae of silkworm as a medium and a case in which a step for hot water extraction of *Paecilomyces tenuipes* powder is included are also preferably considered.

Furthermore, in a method for preparing a cyclic peptide derivative of the present invention, a case in which the cyclic peptide derivative is chemically synthesized is also considered.

It is preferable that a pharmaceutical composition of the present invention includes the cyclic peptide derivative or a salt thereof as an effective component.

Furthermore, in the pharmaceutical composition of the present invention, it is preferable that the composition has an astrocyte proliferative activity.

Furthermore, in the pharmaceutical composition of the present invention, it is preferable that the composition increases an expression amount of NGF gene and VGF gene.

Furthermore, in the pharmaceutical composition of the present invention, it is preferable that the composition has an activity of improving a brain function.

Furthermore, in the pharmaceutical composition of the present invention, it is preferable that the composition has an activity of improving hair texture.

It is preferable that a food product composition of the present invention includes the cyclic peptide derivative or a salt thereof.

Advantageous Effects of Invention

According to the present invention, a novel cyclic peptide derivative which is useful in terms of having a physiological activity including an excellent astrocyte proliferative activity is provided. In addition, with regard to the method for preparing it, it is possible to use, as a raw material, *Paecilomyces tenuipes* which is excellent in terms of cost and stable supply due to easy obtainability.

DESCRIPTION OF EMBODIMENTS

As described above, the cyclic peptide derivative of the present invention is represented by the following general formula (1).

[Chemical Formula 2]

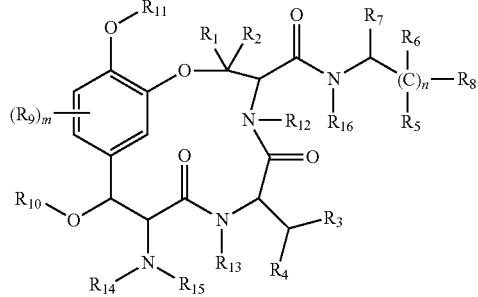

(1)

(in the formula, m is 0 to 3, n≥1, $R_1$ to $R_6$ are a hydrogen atom or a hydrocarbon group, $R_7$ and $R_8$ are a carboxyl group or a salt thereof, or an alkoxycarbonyl group, $R_9$ is a hydrocarbon group, a hydroxyl group, an alkoxy group, or an alkylcarbonyloxy group, $R_{10}$ and $R_{11}$ are a hydrogen atom, a hydrocarbon group, or an alkylcarbonyloxy group, and $R_{12}$ to $R_{16}$ are a hydrogen atom or a hydrocarbon group).

Herein, the hydrocarbon group is linear or branched and saturated or unsaturated, or alicyclic group, and it preferably represents a group with 1 to 6 carbon atoms, and more preferably a group with 1 to 4 carbon atoms. The same also applies to the hydrocarbon part of an alkoxy group, an alkoxycarbonyl group, and an alkylcarbonyloxy group.

Preferred examples thereof include a hydrocarbon group in which the hydrocarbon part is an alkyl group with 1 to 4 carbon atoms.

Examples of the salt of carboxyl group as $R_7$ and $R_8$ include a metal salt like an alkali metal salt and an alkali earth metal salt, and an ammonium salt and an amine salt.

Regarding the above general formula (1), specific examples include any one of those in which $R_1$, $R_2$, $R_3$, and $R_4$ are an alkyl group, in particular, any one of a methyl group and an ethyl group, n=2 to 4, $R_5$ and $R_6$ are a hydrogen atom, $R_7$ and $R_8$ are a carboxyl group, m=0, $R_{10}$ and $R_{11}$ are a hydrogen atom, $R_{12}$ and $R_{13}$ are a hydrogen atom, and $R_{14}$ and $R_{15}$ are a hydrogen atom, and an alkyl group, in particular, a methyl group.

For production of the cyclic peptide derivative of the present invention, collection from *Paecilomyces tenuipes* is preferably made by using various methods of extraction and separation.

Furthermore, for a method of producing the cyclic peptide derivative, it is preferable that *Paecilomyces tenuipes* is the product which is artificially cultured by using pupae of silkworm as medium. Pupae of silkworm may be either raw pupae or dried pupae. In case of using dried pupae, it is possible to use them while maintaining the shape of pupae. It is also possible that pupae powder obtained by preparing dried pupa in powder form are added to a known medium for artificial culture of mushrooms, and used.

Furthermore, according to the method for preparing the cyclic peptide derivative, the production can be made not only by collection from *Paecilomyces tenuipes* but also by combination of various known chemical synthetic methods like peptide synthesis.

Furthermore, derivatization of the cyclic peptide can be achieved by synthesis of a derivative peptide, or by other known methods. For derivatization of the cyclic peptide, a known enzyme method or chemical method can be applied.

Figure 1:
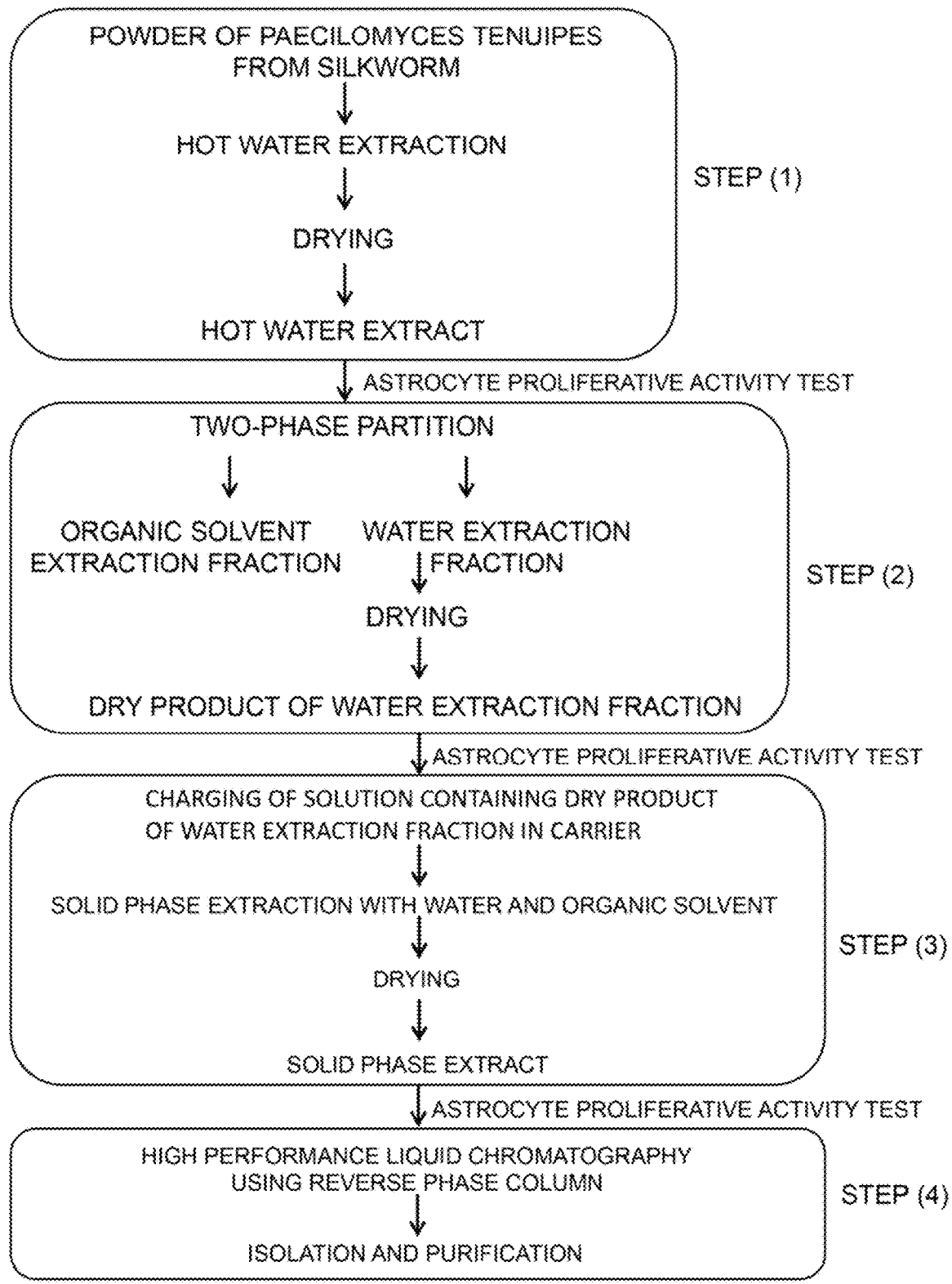
FIG. 1 is a drawing illustrating an outline of the step for isolating and purifying the cyclic peptide derivative of the present invention.

Next, in view of FIG. 1, explanations are given for the method of collecting the cyclic peptide derivative of the present invention, which is expressed by the general formula (1), from *Paecilomyces tenuipes*.

The cyclic peptide derivative of the present invention is isolated and purified by the production method including the following steps:

(1) step for obtaining a hot water extract by drying a hot water extract liquid of *Paecilomyces tenuipes* powder;

(2) step for obtaining a dry product of a water extraction fraction according to separation into a water extraction fraction and an organic solvent extraction fraction, respectively, by performing a two phase distribution using an aqueous solution which contains the hot water extract obtained in the above step (1) and an organic solvent;

(3) step for obtaining a solid phase extract by, after charging a solution containing the dry product of a water extraction fraction obtained in the above step (2) in a carrier, contacting the carrier with a mixture liquid of water and an organic solvent for solid phase extraction, and drying an extract liquid; and (4) step for isolating and purifying the cyclic peptide derivative by separating a solution containing the solid phase extract obtained in the above step (3) by high performance liquid chromatography using a reverse phase column.

Hereinbelow, each step is explained additionally. Incidentally, in each step described below, it is possible to proceed with the isolation and purification while checking that the components having an astrocyte proliferative activity are contained in any of the obtained fractions by carrying out for each obtained fraction the astrocyte proliferative activity test according to the method described in the following examples.

According to the step (1), a hot water extract is obtained by drying a hot water extract liquid of *Paecilomyces tenuipes*.

*Paecilomyces tenuipes* is widely distributed in Japan, Taiwan, China, Nepal, and the like, and as a parasite on pupae and larvae of moths, pupae and larvae of silkworm, or the like, it grows upon taking nutrients from them and produces a pale yellow fruiting body from dead bodies of insects. *Paecilomyces tenuipes* used as a material of the cyclic peptide derivative of the present invention can be naturally found *Paecilomyces tenuipes*, but it is preferably *Paecilomyces tenuipes* which has been artificially cultured by using silkworm as a host. Because *Paecilomyces tenuipes* can be more easily obtained compared to *Cordyceps sinennsis*, the production cost can be saved and also the cyclic peptide derivative can be stably supplied.

Incidentally, the host of *Paecilomyces tenuipes* may be either pupae of *B. mori* or larvae of silkworm. Furthermore, the pupae of silkworm may be either raw pupae or dried pupae. In case of using dried pupae, it is possible to use it while maintaining the shape of pupae. It is also possible that pupae powder obtained by preparing dried pupae in powder form are added to a known medium for artificial culture of mushrooms, and used. For any case of using raw pupae or dried pupae as hosts, the same activity is shown by the extract of *Paecilomyces tenuipes* in the astrocyte proliferative activity test of the examples which will be described later.

Various methods have been suggested as a method for artificial culture of *Cordyceps*. Examples thereof include a method described in Japanese Patent No. 3865735 in which larvae of *B. mori* before forming cocoons are vigorously boiled followed by drying, and after mixing 50 to 90 percent of dry powder of this silkworm larvae with a dry food product consisting of a remaining amount of 1 or more kinds of dry powder of beans, cereals, sea weeds, or mushrooms and addition of a culture solution followed by kneading, the resultant is densely applied on a bottom part of a culture box to produce a medium, which is then sealed in a inoculation bag and heated for sterilization, and plant worm fungus is inoculated to the medium and cultured therein.

Furthermore, according to the present invention, it is preferable to use *Paecilomyces tenuipes* powder which is obtained by freeze drying of *Paecilomyces tenuipes* cultured by the above method, for example, followed by pulverization. Herein, it is sufficient that the *Paecilomyces tenuipes* powder used in the present invention is a powder of only the fruiting body of *Paecilomyces tenuipes*. However, it is preferably a powder including the fruiting body and a host (for example, silkworm).

The method for hot water extraction of *Paecilomyces tenuipes* powder is not particularly limited, but according to solid liquid extraction in which water is added to *Paecilomyces tenuipes* powder and heated by an autoclave or the like, a hot water extract liquid can be obtained. The heating conditions can be suitably designed. For example, by heating for 60 minutes approximately at 80 to 120° C., a hot water extract liquid of *Paecilomyces tenuipes* powder can be obtained. Furthermore, by recovering a filtrate solution according to centrifugation of a hot water extract liquid and filtration of a supernatant, and performing repeatedly the above extraction step, a hot water extract liquid can be obtained at high yield from *Paecilomyces tenuipes* powder. In addition, by collecting a filtrate solution of a supernatant of the hot water extract liquid from *Paecilomyces tenuipes* powder followed by freeze drying, a hot water extract of from *Paecilomyces tenuipes* powder (PTE) can be obtained.

As shown in FIG. 1, in the step (2), according to separation into a water extraction fraction and an organic solvent extraction fraction by performing a two phase distribution using an aqueous solution which contains the hot water extract obtained in the above step (1) and an organic solvent, a dry product of the water extraction fraction is obtained.

According to this step, by performing two phase distribution (i.e., liquid-liquid extraction) using water and an organic solvent, a hot water extract (PTE) of *Paecilomyces tenuipes* can be separated into a water extraction fraction and an organic solvent extraction fraction. Specifically, by dissolving a hot water extract of *Paecilomyces tenuipes* powder in water and adding the solution and an organic solvent into a separatory funnel followed by shaking, a material exchange is allowed to occur at an interface of those two liquids, and then the organic substances or the like that are contained in an aqueous layer can be removed. For such case, examples of the organic solvent include an organic solvent such as n-hexane, ethyl acetate, or acetone, and among them, it is preferable to use ethyl acetate.

Furthermore, by performing a nitrogen gas drying treatment or a freeze drying treatment or the like of the water extraction fraction obtained by the above method, it is possible to have a dry product of the water extraction fraction.

In the step (3), (3) a solid phase extract is obtained by, after charging a solution containing the dry product of a water extraction fraction obtained in the above step (2) in a carrier, contacting the carrier with a mixture liquid of water and an organic solvent for solid phase extraction, and drying an extract liquid.

For this step, various known methods for purification can be adopted. Examples thereof include column (silica gel) chromatography, and in particular, reverse phase flash column chromatography is preferably exemplified. Because a column (silica gel) with fine grains is used and development is carried out by applying pressure to the inside of a column, the reverse phase flash column chromatography has an excellent purification performance.

As a preferred mode, a method in which water (ultra pure water) is applied over a carrier charged (i.e., added) with a solution containing the dry product of a water extraction fraction obtained in the above step (2) to obtain an extract liquid by solid phase extraction, and then, a successive extraction for having extraction of several times while gradually increasing the concentration of a mixture of water and an organic solvent can be exemplified. By performing solid phase extraction according to application of water (ultra pure water) over a carrier charged (i.e., added) with a solution containing the dry product of a water extraction fraction obtained in the above step (2), sugars included in the water extraction fraction can be eluted, and extraction of an effective component by a subsequent solid phase extraction using a mixture liquid of water and an organic solvent can be more surely carried out.

In the step (3), concentration of the organic solvent in a mixture solution is preferably 20% to 80%, more preferably 40% to 70%, and particularly preferably 60% or so. As the concentration of the organic solvent is within the above range in a mixture solution, components having an astrocyte proliferative activity can be purified more certainly. Furthermore, in case of performing successive extraction, after solid phase extraction by application of water (ultra pure water), by carrying out the extraction with gradual increase of the concentration of the organic solvent in a mixture solution like 10%, 20%, 40%, 60% . . . , for example, the effective components can be more certainly extracted. In that case, components having an astrocyte proliferative activity are included in an extract liquid in which concentration of the organic solvent in a mixture solution is 40% to 70%, in particular, 60% or so.

Furthermore, examples of the organic solvent that are used in the step (3) include methanol, ethanol, acetonitrile, acetone, dioxane, tetrahydrofuran, and isopropyl alcohol, and among them, methanol and ethanol may be preferably used. By using methanol or ethanol, the effective components can be certainly extracted.

Furthermore, the extract liquid obtained after the step (3) may be prepared as an extract in solid form after suitably carrying out a treatment including freezing, drying, or the like for condersation drying. Such extract in solid form may be directly used. However, by subjecting it to a next purification step, purification to a single cyclic peptide derivative or a salt thereof can be achieved.

According to the step (4), the cyclic peptide derivative is isolated and purified by separating a solution containing the solid phase extract obtained in the above step (3) based on high performance liquid chromatography using a reverse phase column.

For the step, a purification method known in the art can be adopted. Examples of the reverse phase column to be used include a $C_{18}$, $C_{30}$ column, and in particular, the $C_{30}$ column can be preferably exemplified. Because a modifying group with 30 carbon atoms is formed on a surface of a carrier of a $C_{30}$ column and polarity of the carrier is low, the $C_{30}$ column has an excellent separation performance for a compound with low polarity.

Examples of the organic solvent used in the step (4) include methanol, ethanol, acetonitrile, acetone, dioxane, tetrahydrofuran, and isopropyl alcohol, and among them, methanol and ethanol as a solvent with high polarity may be preferably used. By using methanol or acetonitrile, the effective components can be certainly extracted.

Examples of an aqueous elution liquid that is used for the step (4) include MQ, diethyl bicarbonate buffer solution, or the like.

Figure 2:
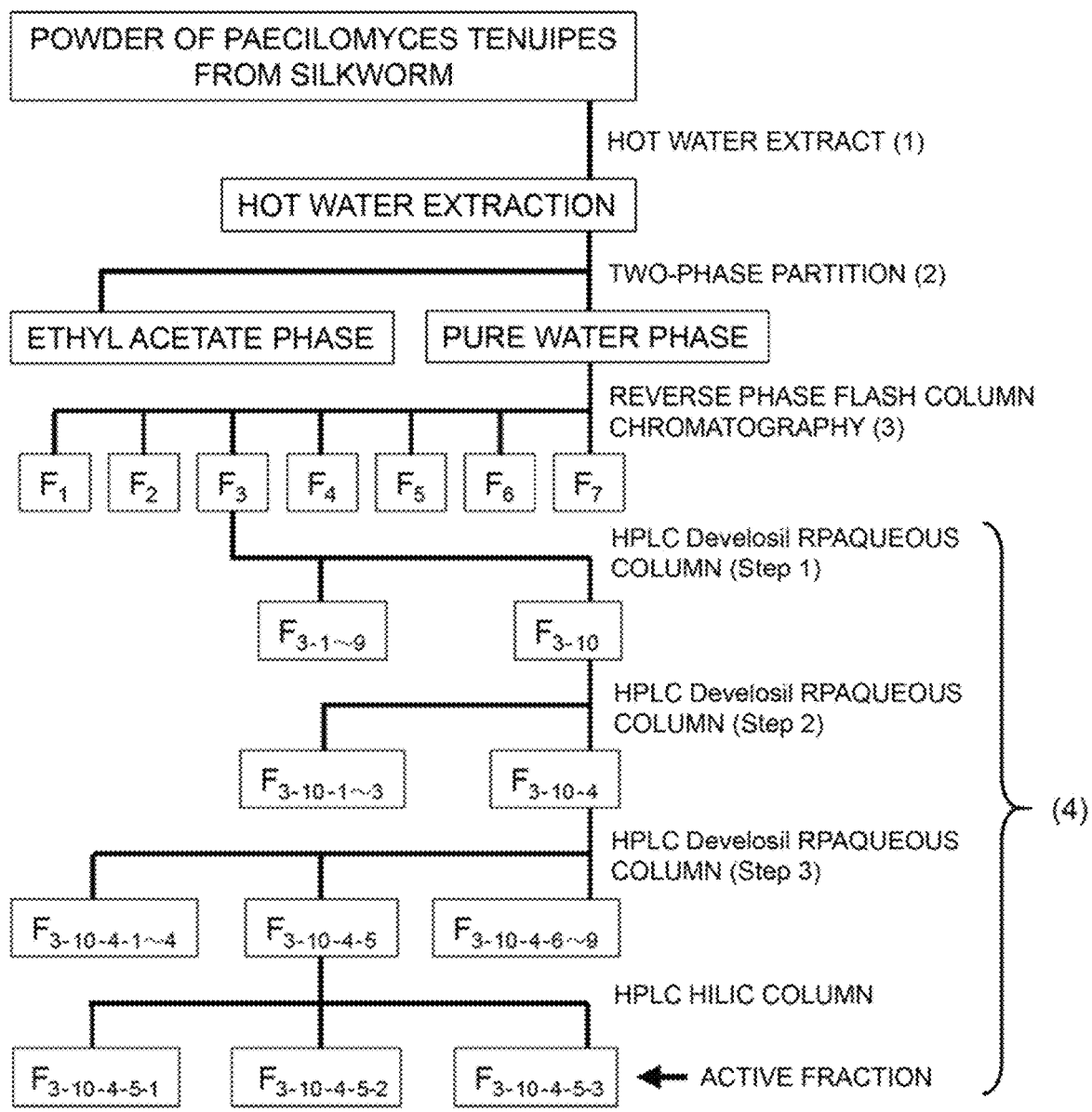
FIG. 2 is a drawing illustrating the step for isolation and purification from *Paecilomyces tenuipes* in Examples of the present invention.
Figure 3:
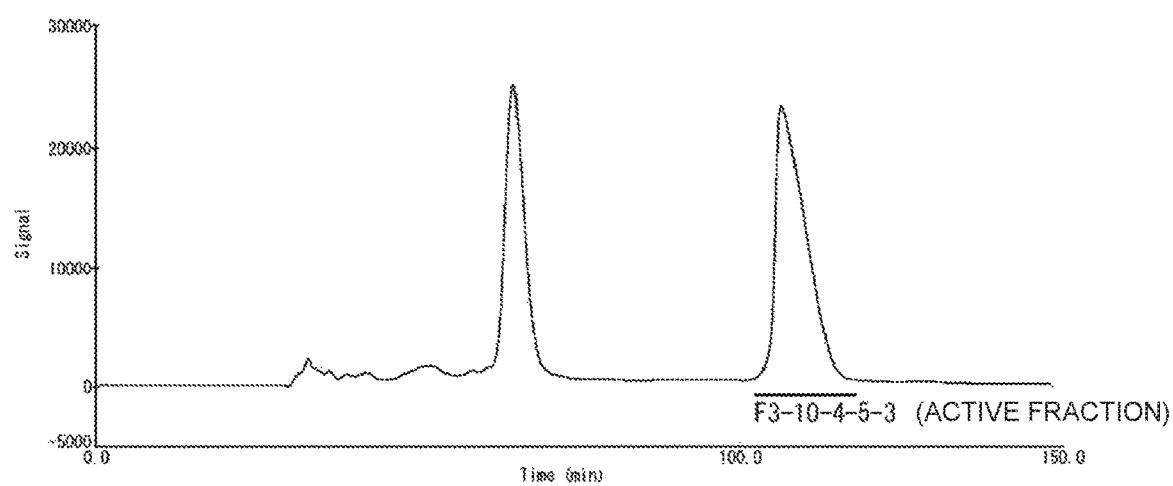
FIG. 3 is a drawing exemplifying the result of isolating the cyclic peptide derivative according to HPLC using HILIC column.

FIG. 2 is a drawing illustrating the step for isolation and purification from *Paecilomyces tenuipes* in Examples of the present invention. As shown in FIG. 2, by having the step (1) to step (4), a peak (F-3-10-4-5-3) containing the cyclic peptide derivative of the present invention that is obtained in Examples to be describe below can be fractionated as shown in FIG. 3, for example.

For the F-3-10-4-5-3 fraction of Examples, an NMR and MS analysis is performed according to the method shown in Examples to be described below, and as a result, the structure of the obtained cyclic peptide derivative is determined to be represented by the following formula (2).

[Chemical Formula 3]

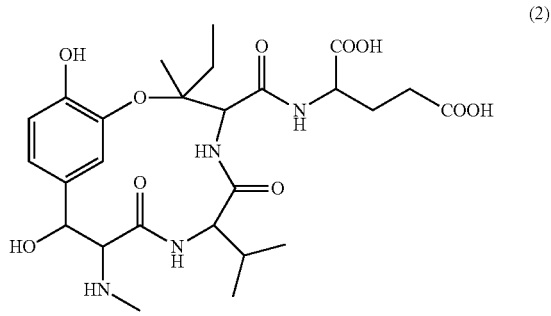

(2)

In the cyclic peptide derivative, a peptide consisting of 4 kinds of amino acids, i.e., N-methyl-β-hydroxy DOPA, valine, β-hydroxyleucine, and glutamic acid represented by the following formula (3) forms a cyclic structure.

[Chemical Formula 4]

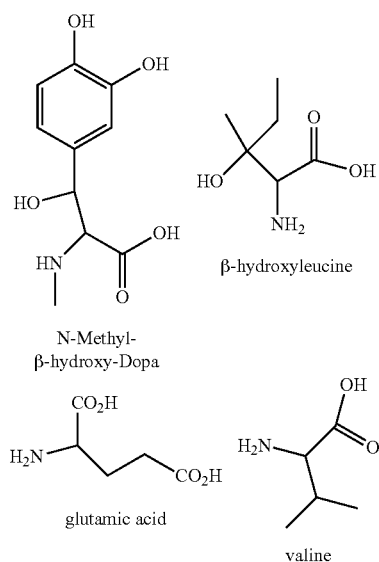

As a result of an NMR analysis and an MS analysis, the cyclic peptide derivative was found to be a water soluble cyclic peptide derivative with molecular weight of 566.2588. Furthermore, as a result of performing a search of the cyclic peptide derivative structure against Scifinder as a chemical structure database of chemical substances, the derivative has been confirmed to be a novel compound.

The cyclic peptide derivative of the present invention or a salt thereof can be used as an effective component of a pharmaceutical composition.

It is also possible that the cyclic peptide derivative of the present invention or a salt thereof is contained in a food product composition.

By having the cyclic peptide derivative of the present invention or a salt thereof act on brain cells either in vivo or in vitro, proliferation of an astrocyte can be achieved. As such, the cyclic peptide derivative of the present invention or a salt thereof can be used for treatment, prevention, or the like of various diseases or disorders.

Because an astrocyte makes up about a half of the entire cells in human brain, the cyclic peptide derivative of the present invention or a salt thereof can be used as a therapeutic agent for cerebral contusion or the like, for example. Furthermore, because an astrocyte has a function of forming a neural network or the like, the cyclic peptide derivative of the present invention or a salt thereof can be used as a therapeutic agent for a cerebral disorder causing a cognitive function disability, for example, Alzheimer's disease and Parkinson's disease. Furthermore, because an astrocyte is involved with memory formation, the cyclic peptide derivative of the present invention or a salt thereof can be used for improvement of memory ability or learning ability like supplementation of space pattern or information. Furthermore, as a decrease in the number of astrocytes is commonly shown in a mental disorder like schizophrenia, bipolar disorder, and depression, (Non Patent Literature 28), the cyclic peptide derivative of the present invention or a salt thereof can be also used as a therapeutic agent for those mental disorders.

The cyclic peptide derivative of the present invention or a salt thereof can be administered either orally or parenterally.

In case of oral administration, it may have a shape including a tablet, a pill, a powder, a troche, a separately wrapped package, an oblate, an elixir, a suspension, an emulsion, a liquid, syrup, an aerosol, and a sterile packaged powder. In that case, a vehicle, a wetting agent, an emulsifying agent, a dispersing agent, a preservative, a sweetening agent, a flavoring agent, or the like that are commonly known in the field may be also suitably added as an additive. Examples thereof include lactose, dextrose, sucrose, sorbitol, mannitol starch, gum Arabic, calcium phosphate, alginate salt, tragacanth, gelatin, calcium silicate, microcrystalline cellulose, polyvinyl pyrrolidone, cellulose, water, syrup, and methyl cellulose. In case of oral administration, the dosage can be suitably determined in consideration of a method for formulation, an administration method, and age, body weight, or the like of a subject for administration. Furthermore, the cyclic peptide derivative of the present invention can be used not only for a pharmaceutical product but also for a health supplement or the like.

Furthermore, in case of parenteral administration, direct administration into a brain can be made in addition to intravenous administration, subcutaneous administration, intradermal absorption, or the like. In case of the direct administration into a brain, an area in a brain can be suitably selected depending on the treatment, symptoms to be improved, or the like.

Furthermore, the cyclic peptide derivative of the present invention or a salt thereof can be administered not only to a human but also to various animals. The animals described herein include a mammal including human, and birds like poultry that are consumed as food. Examples of the mammal include, in addition to human, a test animal like monkey, mouse, rat, rabbit, goat, and sheep, livestock like pig, cow and horse, and a companion animal like dog and cat. Furthermore, examples of the poultry include a chicken and a quail.

As for the concentration of the cyclic peptide derivative of the present invention at which astrocyte proliferative activity is exhibited in an in vitro experimental system, concentration in the range of 0.1 μM or more and 50 μM or less, preferably 1 μM or more and 50 μM or less, and more preferably 1 μM or more and 25 μM or less is exemplified. Furthermore, with regard to an in vivo system, the oral administration concentration of the cyclic peptide derivative of the present invention as an astrocyte proliferation agent is, for example, in the range of 0.1 μg/kg or more and 50 μg/kg or less, preferably 1 μM or more and 50 μM or less, and more preferably 1 μM or more and 25 μM or less per day for a mammal including human.

Furthermore, the cyclic peptide derivative of the present invention or a salt thereof can enhance an expression amount of NGF gene and VGF gene.

Furthermore, the cyclic peptide derivative of the present invention or a salt thereof can be used as an agent for improving the cerebral function.

Furthermore, the cyclic peptide derivative of the present invention or a salt thereof can be used as an agent for improving hair texture.

The cyclic peptide derivative of the present invention or a salt thereof has an excellent astrocyte proliferative effect, and can be effectively used for various applications that are described above. Furthermore, because the cyclic peptide derivative of the present invention or a salt thereof is obtained from, as a raw material, *Paecilomyces tenuipes* that can be more easily obtained than *Cordyceps sinennsis*, it is excellent in terms of cost and stable supply.

It has been demonstrated that "development of new glia drugs" for controlling the function of glial cells including an astrocyte or having as a target a molecular group in which the glial cells are strongly expressed is important in the study for developing a new drug in future (Non Patent Literature 29). There is a possibility that the cyclic peptide derivative of the present invention or a salt thereof becomes one good example of "development of new glia drugs".

EXAMPLES

Examples of the present invention are explained hereinbelow, but the present invention is not limited to the following Examples.

I. Isolation and purification of components having astrocyte proliferative activity <1> Isolation and Purification Step FIG. 2 is a drawing illustrating the step for isolation and purification from *Paecilomyces tenuipes* in Examples of the present invention. The step for isolating and purifying a cyclic peptide derivative includes four steps of (1) step for hot water extraction from *Paecilomyces tenuipes*, (2) step for fractionation based on two phase distribution of hot water extract (PTE), (3) step for fractionation by reverse phase flash column chromatography, and (4) step for purification by reverse phase high performance chromatography (RP-HPLC). Each step of those (1) to (4) corresponds to each of the step (1) to the step (4) that are shown in the outline diagram of FIG. 1.

[A] Methods

Hereinbelow, operations in each step of the (1) to (4) are explained in detail in view of FIG. 2.

(1) Hot Water Extraction from *Paecilomyces tenuipes* Powder

As for the *Paecilomyces tenuipes* powder of *B. mori Cordyceps* which is used for isolation/purification and structure determination of a compound having an astrocyte proliferative activity, the powder provided by Tohaku Nosan Kigyo Kumiai in Fukushima Ken, Japan was used.

To *Paecilomyces tenuipes* powder (42 g), 10 times (w/v) its amount of distilled water (420 ml) (hereinbelow described as MQ) was added, and according to heating at 120° C. for 20 minutes in an autoclave, a hot water extract was obtained. After that, the hot water extract was filtered by a qualitative filter paper (No. 2 ADVANTEC) and collected (liquid A), and by adding again 10 times its amount of MQ (420 ml) to the residuals after the filtration, the second extraction and filtration were performed at the same conditions (liquid B). The liquid A and the liquid B were admixed with each other, filtered again, and subjected to freeze drying using a freeze dryer (EYELA FDU-2100, manufactured by Tokyo Rikakikai). The obtained powder was used as *Paecilomyces tenuipes* hot water extract (hereinbelow, described as PTE), and stored in an ultralow temperature bath at −80° C. until use.

For the obtained PTE, the physiological activity was determined based on an astrocyte proliferative activity test which will be described later. Accordingly, it was confirmed that components having an astrocyte proliferative activity are contained in the PTE.

(2) Fractionation Based on Two Phase Distribution of PTE

To 6 g of the PTE powder obtained from the step (1), 50 times its amount (w/v) (300 ml) of MQ was added for dissolution, and then transferred to a separatory funnel. By shaking the separatory funnel, even concentration distribution of PTE was established, and then 300 ml of ethyl acetate was added thereto. After repeating the shaking and gas discharge 10 minutes thereafter, the separatory funnel was allowed to stand for 60 minutes to have a separation into 2 layers. MQ layer (MQ-1) as a bottom layer was collected, and to the separatory funnel in which the ethyl acetate layer remains, 300 ml of fresh distilled water was added and the same operations as above were repeated. The aqueous layer (MQ-2) as a bottom layer and the ethyl acetate layer (EA-1) as an upper layer were collected, and after addition of MQ-1 which has been collected first and 300 ml of ethyl acetate to the separatory funnel, the same operations as above were repeated. The MQ layer (MQ-1) as a bottom layer and the ethyl acetate layer (EA-2) as an upper layer were collected. A mixture of MQ-1 and MQ-2 which was then admixed with the MQ fraction, EA-1, and EA-2 of two phase system was used an ethyl acetate fraction of two phase distribution. Each fraction was subjected to condensation drying by using a series of rotary evaporators (CCA-1100, DPE-1220, SB-1000, N-1000, EYELA DTU-20, ULVAC) and a freeze dryer (EYELA FDU-2100), and the obtained powder was collected as a MQ layer extract of two phase distribution and an ethyl acetate extract of two phase distribution, and stored in an ultralow temperature bath at −80° C. until use.

The MQ layer extract of two phase distribution and ethyl acetate extract of two phase distribution obtained above were determined with their physiological activity based on an astrocyte proliferative activity test which will be described later, and it was also confirmed that components having an astrocyte proliferative activity are contained in the MQ layer extract of two phase distribution.

(3) Fractionation by Reverse Phase Flash Column Chromatography

1) Preparation of Reverse Phase Flash Column

For further purification of the MQ layer extract of two phase distribution which has been obtained in the above step (2), reverse phase flash column chromatography was carried out. The column was prepared by a dry type filling method. Silica gel (Wakosil 40C18, Wako Pure Chemical Industries, Ltd.) as a carrier was added to a flash chromatography column so as to have a column volume of 160 cm$^3$, and after swelling by methanol and adding MQ as an initial development solution to the top part of a 500 ml chromatography column, substitution of the solvent and air inside the carrier was carried out by extrusion with an application of pressure using a pump (HIBLOW AIR POMP, Type SPP-6EBS, TECHNO TAKATSUKI CO., LTD.).

2) Fractionation by Reverse Phase Flash Column Chromatography 3.5 mg of MQ layer extract of the two phase distribution was dissolved in 14 ml of MQ, and charged onto the carrier surface of the prepared column. While applying pressure by using a pump, 500 ml of MQ, and 300 ml of 10% methanol (methanol/MQ (1/9, v/v)), 20% methanol (methanol/MQ (1/4, v/v)), 40% methanol (methanol/MQ (2/3, v/v)), 60% methanol (methanol/MQ (3/2, v/v)), 80% methanol (methanol/MQ (4/1, v/v)), and 100% methanol was allowed to flow in order. Each of the eluted fraction was subjected to concentration drying by using a series of rotary evaporators (CCA-1100, DPE-1220, SB-1000, N-1000, EYELA DTU-20, ULVAC) and a freeze dryer (EYELA FDU-2100). Each of the obtained fraction was taken as F1: MQ extraction fraction, F2: 10% methanol extraction fraction, F3: 20% methanol extraction fraction, F4: 40% methanol extraction fraction, F5: 60% methanol extraction fraction, F6: 80% methanol extraction fraction, and F7: 100% methanol extraction fraction, and then stored in an ultralow temperature bath at −80° C. until use.

Each fraction of the obtained F1 to F7 was determined with their physiological activity based on an astrocyte proliferative activity test which will be described later, and it was also confirmed that components having an astrocyte proliferative activity are contained in the F3 fraction.

(4) Purification by Reverse Phase High Performance Liquid Chromatography (RP-HPLC)

For the F3 fraction obtained in the above step (3), purification with three steps including Step 1 to 3 using reverse phase high performance liquid chromatography (RP-HPLC) and a Develosil column and purification using a HILIC, i.e., purification of 4 steps in total, were carried out.

1) Conditions for Analysis

Purification using a Develosil column used in Step 1 to 3 was carried out at the following conditions for analysis.

(Step 1) Column: Develosil RPAQUEOUS (20.0 ID×250 mm) (NOMURA CHEMICAL CO., LTD.), column temperature: 40° C., mobile phase: MQ, methanol, flow rate: variable according to time, time program (% indicates the ratio of methanol in mobile phase): (0 min-60 min) 1.0%, 5.0 ml/min, isocratic→(60 min-180 min) 1.0%-30.4%, 2.0 ml/min, gradient→(180 min-212 min) 30.4%-100.0%, 5.0 ml/min, gradient→(212 min-292 min) 100.0%, 5.0 ml/min, isocratic, end, detection wavelength: 254 nm.

(Step 2 and 3) column: Develosil RPAQUEOUS (20.0 ID×250 mm) (NOMURA CHEMICAL CO., LTD.), column temperature: 40° C., mobile phase: MQ containing 0.01% acetic acid, methanol containing 0.01% acetic acid, flow rate: 5.0 ml/min, time program (% indicates the ratio of methanol containing 0.01% acetic acid in mobile phase): (0 min-30 min) 1.0%, isocratic→(30 min-70 min) 1.0%-40.0%, gradient→(70 min-100 min) 100.0%, isocratic, end, detection wavelength: 254 nm.

(HILIC) column: HILIC (4.6 ID×250 mm) (COSMOSIL), column temperature: 28° C., mobile phase A: 20 mM $Et_2NH$—$CO_2$ buffer (pH 7.0), mobile layer B: $CH_3CN$ (A:B=90:10) isocratic, flow rate: 1.0 ml/min, detection wavelength: 210 nm.

2) Collection of Fractions

According to the separation and purification based on each analysis condition described above, the waveform of a chromatogram was determined, and fractionate collection was made for each peak. In Step 1, the F3 fraction obtained in the step (3) above was fractionated into 10 fractions of F-3-1 to F3-10, and according to an astrocyte proliferative activity test which will be described later, the physiological activity was determined, and the F-3-10 fraction containing the components with an astrocyte proliferative activity was collected by fractionation. In Step 2, the F-3-10 fraction obtained in Step 1 was fractionated into 4 fractions of F-3-10-1 to F3-10-4, and according to an astrocyte proliferative activity test which will be described later, the physiological activity was determined, and the F-3-10-4 fraction containing the components with an astrocyte proliferative activity was collected by fractionation. In Step 3, the F-3-10-4 fraction obtained in Step 2 was fractionated into 9 fractions of F-3-10-4-1 to F-3-10-4-9, and according to an astrocyte proliferative activity test which will be described later, the physiological activity was determined, and the F-3-10-4-5 fraction containing the components with an astrocyte proliferative activity was collected by fractionation. By HILIC, the F-3-10-4-5 fraction obtained in Step 3 was fractionated into 3 fractions of F-3-10-4-5-1 to F-3-10-4-5-3, and according to an astrocyte proliferative activity test which will be described later, the physiological activity was determined, and the F-3-10-4-5-3 fraction containing the components with an astrocyte proliferative activity was collected by fractionation. Each of the obtained fraction was subjected to concentration drying by using one type of a rotary evaporator (CCA-1100, DPE-1220, SB-1000, N-1000, EYELA DTU-20, ULVAC) and a freeze dryer (EYELA FDU-2100), and then a final purified product was obtained as a dietylamine salt.

The obtained final purified product was determined for a physiological activity based on an astrocyte proliferative activity test which will be described later, and it was also confirmed that components having an astrocyte proliferative activity are contained in the F3-10-4-5-3 fraction in the final purified product that is shown in FIG. 3.

[B] Results

As explained in detail in the above, as a result of performing the 7 steps (hot water extraction, two phase distribution, reverse phase flash chromatography, 3 time repetition of high performance liquid chromatography (HPLC) using C30RPAQUEOUS column (Step 1 to Step 3), and HPLC using HILIC column) by using 42 g of the dry powder of B. mori Cordyceps Paecilomyces tenuipes, the F3-10-4-5-3 fraction was obtained as a component having a significant astrocyte proliferative activity from three fractions of the F3-10-4-5-1 to F3-10-4-5-3 which have been separated by HPLC as a final step, as it is shown in FIG. 3. Yield (%) of the extract at each purification step of above 7 steps is described in Table 1.

TABLE 1

| Purification method | Yield (%) |
| --- | --- |
| (a) Dry powder of Paecilomyces tenuipes from silkworm as a starter | 100.00 |
| (b) Hot water extract (PTE) | 27.20 |
| (c) MQ phase of two phase distribution | 25.50 |
| (d) Reverse phase flash column chromatography | 2.01 |
| (e) HPLC Develosil ® C30 RPAQUEOUS Column (Step 1) | 0.57 |
| (f) HPLC Develosil ® C30 RPAQUEOUS Column (Step 2) | 0.08 |
| (g) HPLC Develosil ® C30 RPAQUEOUS Column (Step 3) | 0.07 |
| (h) HPLC COSMOSIL ® HILIC Column | 0.03 |

The amount of the isolated purified product was 1.2 mg and the yield was 0.03%. Incidentally, the biological activity assay in each step was carried out by having the following astrocyte proliferative activity as an indicator.

<2> Astrocyte Proliferative Activity Test

1) Materials for Test

A pregnant ICR female mouse was purchased from Japan SLC, Inc., and a neonatal mouse 24 to 48 after birth was used for the test.

2) Primary Culture of Neonatal Mouse Cerebral Neuronal Cells

A neonatal ICR mouse (24 to 48 after birth) was sufficiently sterilized with 70% ethanol, immersed in 30 ml of PBS (−) in a 100 mm dish (diameter of 100 mm, Orange Scientific) for cell culture, and then placed in a clean bench. The neonatal mouse was subjected to cervical dislocation using tweezers and euthanized. Head of the neonatal mouse was open and the entire brain was removed. The obtained brain was transferred to a 100 mm dish for cell culture in which 15 ml of high glucose Dulbecco's modified Eagle medium (HG-D-MEM, Wako Pure Chemical Industries, Ltd.) is added. By using tweezers, the olfactory bulb, median eminence, and meninges were removed in the medium to obtain only a cerebrum having hippocampus. Subsequently, the obtained cerebrum was transferred to a 100 mm dish for cell culture added with 10 ml of HG-D-MEM, and using a scalpel, the cerebrum was finely cut to be 1 $mm^2$ or less. The cerebrum after cutting was transferred, together with the medium, to a 50 ml conical tube (TPP), and after allowing it to stand for 2 minutes, the supernatant was removed. Subsequently, the cerebrum after cutting was added with 4 ml of fresh HG-D-MEM, and after further adding 400 μl of 2.5% trypsin (SIGMA) and 40 μl of 1% DNase I (SIGMA), the cerebrum was incubated in a water bath at 37° C. for 10 minutes under intermittent stirring. Subsequently, to the cerebrum after cutting, 10 ml of HG-D-MEM (10% FBS) was added to terminate the reaction of trypsin followed by centrifuge for 3 minutes at 1,000×g using a centrifuge (H-9R, KOKUSAN Co., Ltd.). The supernatant was collected by an electric pipette, 10 ml of HG-D-MEM (10% FBS) was added to a precipitated cell mass, and pipetting using a sterile pipette was carried out several times until the cell mass is not observed. To remove the remaining cell mass from this cell dispersion, the cell dispersion was passed through a cell strainer (pore diameter of 100 μm, BD Falcon™), and the number of cells in the cell dispersion which has passed through the cell strainer was counted by using a cell counting plate. An adjustment was made with HG-D-MEM (10% FBS) such that the number of cells is $6.0 \times 10^5$ cells/ml. After the adjustment of the number of cells, the cell dispersion was seeded, in an amount of 7 ml for each, to a Poly-D-Lysine Cellware 100 mm Dish (PDL 100 mm dish, BD Falcon™). 96 Hours after the seeding, the medium was removed once using an aspirator, and after briefly washing the inside of a 100 mm PDL dish with 10 ml of PBS (−), the medium exchange was carried out by newly adding 7 ml of HG-D-MEM. The above method and the astrocyte preparation described below were carried out based on the method of McCarthy and de Vellis (1980, Non Patent Literature 30).

3) Preparation of Astrocyte

72 Hours after the medium exchange, the 100 mm PDL dish seeded with the cell broth was removed from the incubator, and tightly covered using a parafilm and fixed by overlaying 3 to 4 dishes. The resultant was cultured by shaking using a bioshaker (MULTI SHAKER MMS, INCUBATOR FMS/EYELA) under a condition including 37° C., 100 rpm, and 20 hours, and the neuronal cells, cell debris, dead cells or the like were liberated. At that time, in the inside the 100 mm PDL dish, only the astrocyte as a glial cell in central nervous system other than neuron was adhered (hereinbelow, described as culture astrocyte). After the shaking, the 100 mm PDL dish was transferred to a clean bench, the supernatant was removed by an aspirator and washed with 10 ml of PBS (−), and after adding 1 ml of 2.5% trypsin (SIGMA) using a Pasteur pipette, the dish was left to stand in an incubator for 10 minutes. The 100 mm PDL dish was again brought back to the clean bench, and added with 10 ml of Dulbecco's modified Eagle medium (D-MEM, Wako Pure Chemical Industries, Ltd.) (10% FBS). After terminating the reaction of trypsin, the cell broth was collected in a 50 ml conical tube. After that, the number of cells was counted using a cell counting plate, and an adjustment was made with D-MEM (10% FBS) such that the number of cells is $1.5 \times 10^5$ cells/ml. The resulting astrocyte cell broth was seeded in an amount of 7 ml to the 100 mm PDL dish.

4) Subculture of Culture Astrocyte

The culture astrocyte which has been prepared in the above 3) was cultured for 2 weeks by performing medium exchange at every 72 to 96 hours after the seeding. The operations are basically the same as the medium exchange of above experiment except that D-MEM (10% FBS) is used as a medium. 14 Days later, culture under shaking using a bioshaker was not performed, and after that, the number of culture astrocyte cells was adjusted according to the adjustment method of above 3) and then subculture was carried out.

5) Activity Test

By using the culture astrocyte after subculture which has been obtained as above (i.e., at secondary subculture), the same astrocyte proliferative activity test as above was carried out. As a result, as shown in FIG. 3, it was confirmed that the F3-10-4-5-3 fraction contains components which exhibit an astrocyte proliferative activity.

6) Test for Identifying Primary Culture Astrocyte and Determination of Characteristics of Obtained Cells To exclude the possibility of contamination of microglia or oligodendrocyte derived from neuronal cells or glia cells in the primary culture astrocyte or the secondary subculture astrocyte, an immunohistochemical analysis was carried out by using an antibody specific to each cell described above.

Namely, by using the astrocyte of the secondary subculture, a cell suspension was prepared in the same order as above 3) such that the cell concentration is $3 \times 10^4$ cells/ml. As a medium, LG-D-MEM (10% FBS) was used. To a 35 mm dish (BD Falcon) of which surface is coated with laminin (SIGMA-Aldrich, 1 μg/cm² culture area) and fibronectin (SIGMA-Aldrich, 3 μg/cm² culture area), the cell suspension of the prepared culture astrocyte was added at 2 ml/dish followed by culture according to incubation at conditions of 37° C., 5.0% $CO_2$. 24 Hours after the start of the culture, the medium inside the dish was replaced with LG-D-MEM (0% FBS) to suppress proliferation of the astrocyte cells. Furthermore, after culture for 24 hours at conditions of 37° C., 5.0% $CO_2$, the medium inside the dish was replaced with the same medium as above, i.e., LG-D-MEM (0% FBS), in which the cyclic peptide derivative of which structure has been determined after isolation and purification is dissolved in advance to have the cyclic peptide derivative concentration of 25 μM. Then, the astrocyte was exposed to the cyclic peptide derivative for 0 hour or 24 hours at conditions of 37° C., 5.0% $CO_2$. As a control group, LG-D-MEM (0% FBS) not added with any cyclic peptide derivative was used.

Whole medium was removed from the dish of each treatment group by aspiration. After adding a PBS solution containing 4% paraformaldehyde (Wako) and shaking for 15 minutes at room temperature, the cells were fixed. Then, a PBS solution containing 0.1% Triton® X-100 (SIGMA-Aldrich) was added and an infiltration treatment was carried out by shaking for 5 minutes. After the infiltration treatment, Image-iT FX Signal Enhancer (life technologies) was added and, according to shaking for 1 hour at room temperature, a blocking treatment was carried out.

Subsequently, for identification of cells, each antibody shown in Table 2 was added as a primary antibody to the cells after the blocking treatment followed by shaking for 1 hour at room temperature. For detection of the primary antibody, a secondary antibody (Invitrogen) conjugated with Alexa Fluor 488- or Alexa Fluor 546—as a fluorophore was used, and after the addition of the secondary antibody, shaking at room temperature was carried out for 30 minutes. The fluorescent image was observed and photographed by using a fluorescent microscope IX71 (Olympus). The observation results are shown in Table 3.

TABLE 2

| Cell type | Antibody name | Immunized animal | Manufacturer |
|---|---|---|---|
| Neuron | Anti-MAP2 | Chicken | abcam |
| Astrocyte | Anti-EAAT2 | Sheep | abcam |
| Microglia | Anti-NG2 | Mouse | abcam |
| Oligodendrocyte | Anti-MBP | Mouse | abcam |

TABLE 3

| Cell type | Antibody name | Cells exhibiting positive reaction (%) |
|---|---|---|
| Neuron | Anti-MAP2 | 0 |
| Astrocyte | Anti-EAAT2 | >99 |
| Microglia | Anti-NG2 | <1 |
| Oligodendrocyte | Anti-MBP | 0 |

As shown in Table 3, the astrocyte used in Examples exhibited a negative reaction for Anti-NG2 specific to microglia cell, Anti-MBP specific to oligodendrocyte cell, and Anti-MAP2 specific to neuronal cell, and the astrocyte exhibits a positive reaction only for a glia type glutamic acid transporter (referred to as EAAT2 or GLT-1). Considering that EAAT2 is expressed in an astrocyte among the cells of a central nervous system, it was confirmed that the culture astrocyte derived from a brain consists only of an astrocyte with purity of 99% or higher.

II. Determination of Chemical Structure of Components Having Astrocyte Proliferative Activity

[A] Methods

By using a sample which has been obtained by collecting and freeze drying the F3-10-4-5-3 fraction that has been finally isolated and purified in the step (4) for isolation and purification of the components having an astrocyte proliferative activity, the chemical structure of the F3-10-4-5-3 fraction was determined based on an NMR analysis and an MS analysis. For the NMR analysis, Brucker Avance 600 was used. For the MS analysis, JEOL JMS-AX500 was used. The optical rotation was measured by using JASCO P-1030 polarimeter with a sodium lamp (D line).

[B] Results

Figure 4:
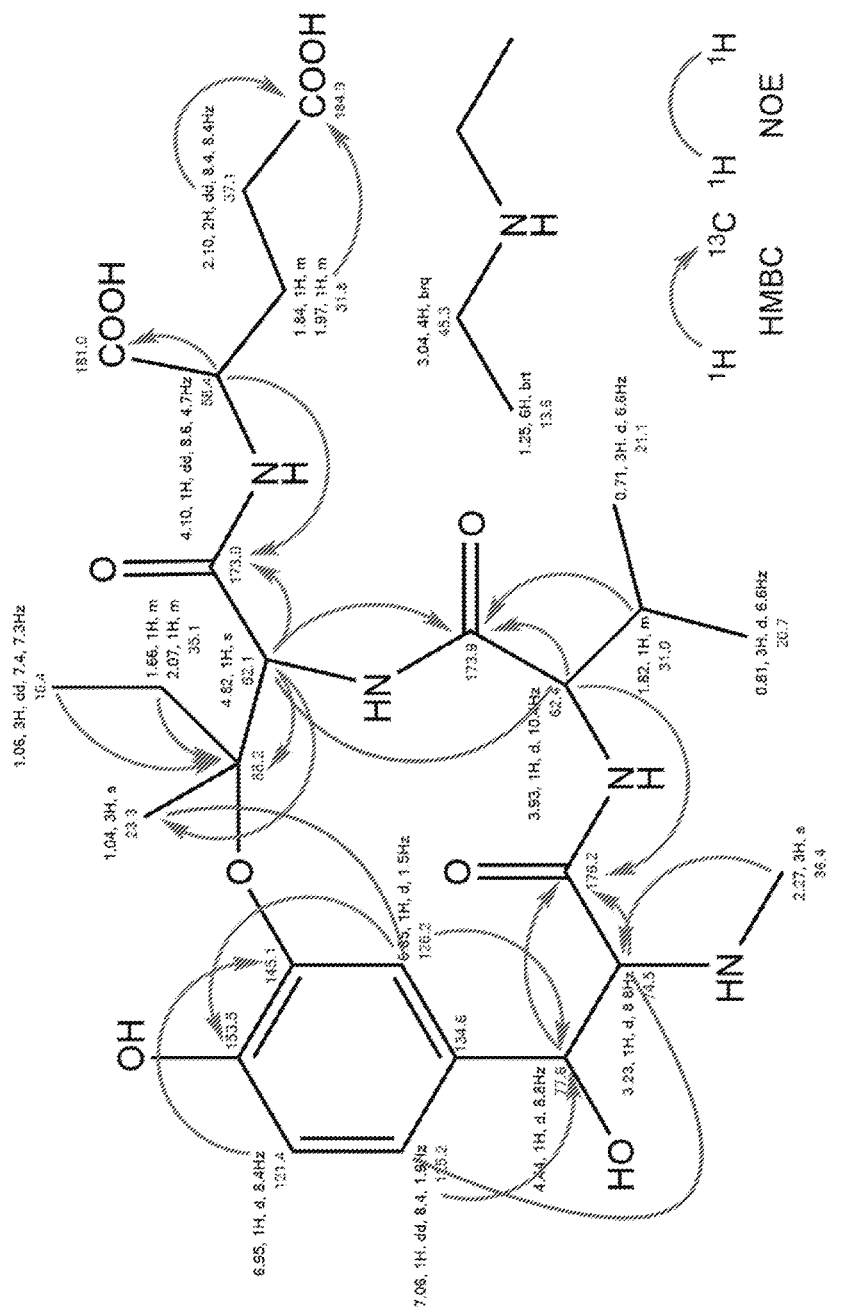
FIG. 4 is a drawing exemplifying the result of HMBC analysis by $^1$H-NMR of the cyclic peptide derivative of the present invention.
Figure 5:
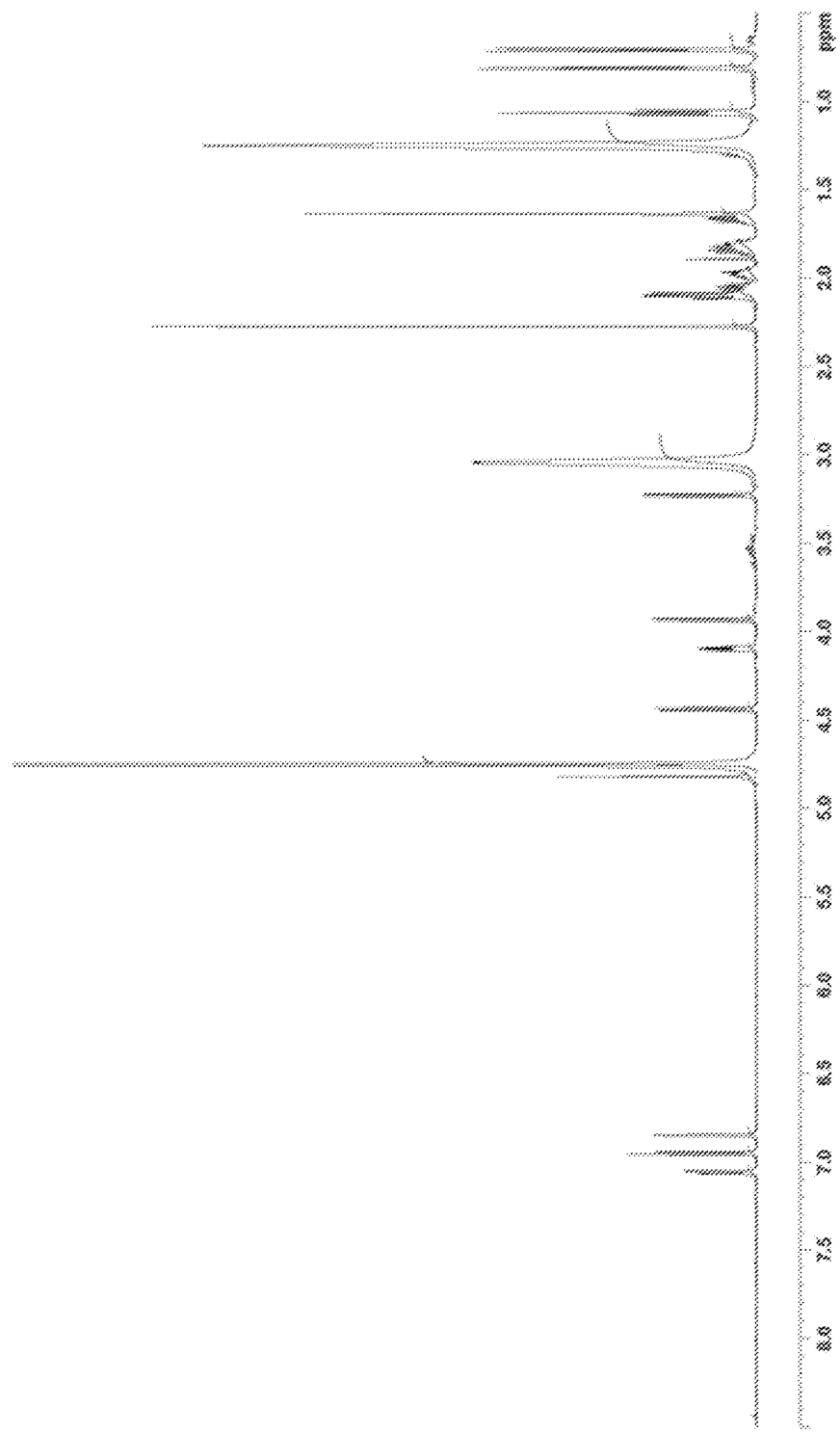
FIG. 5 is a drawing illustrating a $^1$H-NMR spectrum of the cyclic peptide derivative of the present invention.

According to the analysis, it was identified as the cyclic peptide derivative which is represented by the formula (2). The result of HMBC analysis based on $^1$H-NMR is exemplified in FIG. 4. Furthermore, the $^1$H-NMR spectrum of the cyclic peptide derivative was exemplified in FIG. 5. Chemical shift of each peak of $^1$H-NMR of the cyclic peptide derivative is as shown in Table 4, and chemical shift of each peak of $^{13}$C-NMR is as shown in Table 5.

TABLE 4

| $^1$H-NMR 600 Hz (D$_2$O) | | | |
|---|---|---|---|
| 3-H | 4.82 (1H, s) | 19''-H | 2.10 (2H, dd, J = 8.4, 8.4 Hz) |
| 6-H | 3.93 (1H, d, J = 10.4 Hz) | 21-H | 1.04 (3H, s) |
| 9-H | 3.23 (1H, d, J = 8.8 Hz) | 22-H | 1.66 (1H, m) |
| 9-NCH$_3$ | 2.27 (3H, s) | | 2.07 (1H, m) |
| 10-H | 4.44 (1H, d, J = 8.8 Hz) | 23-H | 1.06 (3H, t, J = 7.34 Hz) |
| 12-H | 7.06 (1H, dd, J = 8.4, 1.9 Hz) | 24-H | 1.82 (1H, m) |
| 13-H | 6.95 (1H, d, J = 8.4 Hz) | 25-H | 0.71 (3H, d, J = 6.6 Hz) |
| 16-H | 6.85 (1H, d, J = 1.9 Hz) | 26-H | 0.81 (3H, d, J = 6.6 Hz) |
| 19-H | 4.10 (1H, dd, J = 8.6, 4.7 Hz) | (CH$_3$CH$_2$)$_2$NH | 3.04 (4H, m) |
| 19'-H | 1.97 (1H, m) | (CH$_3$CH$_2$)$_2$NH | 1.25 (6H, m) |
| | 1.84 (1H, m) | | |

TABLE 5

| $^{13}$C-NMR (150 MHz, D20) | | | |
|---|---|---|---|
| C-2 | 88.2 | C-17 | 173.0 |
| C-3 | 62.1 | C-19 | 58.4 |
| C-5 | 173.9 | C-19' | 31.8 |
| C-6 | 62.4 | C-19'' | 37.1 |
| C-8 | 176.2 | C-20 | 184.9 |
| C-9 | 74.5 | C-20' | 181.0 |
| 9-NCH$_3$ | 36.4 | C-21 | 23.3 |
| C-10 | 77.6 | C-22 | 35.1 |
| C-11 | 134.6 | C-23 | 10.4 |
| C-12 | 125.2 | C-24 | 31.0 |
| C-13 | 121.4 | C-25 | 20.1 |
| C-14 | 153.5 | C-26 | 203 |
| C-15 | 145.1 | (CH$_3$CH$_2$)$_2$NH | 45.3 |
| C-16 | 126.2 | (CH$_3$CH$_2$)$_2$NH | 13.6 |

Furthermore, as an MS analysis, an analysis based on FAB-MS was carried out. The analysis conditions and analysis results are as described below.

MS: FAB negative, matrix: glycerol, HRMS (FAB) m/z (M-H)$^-$, calcd. for [C$_{26}$H$_{37}$N$_4$O$_{10}$—H]$^-$ 565.2510, found 565.2512.

$[\alpha]^{17.4}_D = -21.6°$ (c=0.18, H$_2$O)

As a result of the NMR analysis and MS analysis, the cyclic peptide derivative of the present invention with an astrocyte proliferative activity was found to be a novel water soluble cyclic peptide derivative having molecular weight of 566.2588. As a result of performing a search of the cyclic peptide derivative structure against Scifinder as a chemical structure database of chemical substances, the derivative has been confirmed to be a novel compound.

III. Functional Analysis of Novel Cyclic Peptide Derivative

<1> Functional Analysis of Culture Astrocyte Proliferative Activity

1. Culture Astrocyte Proliferation Promoting Activity

[A] Methods

By using an astrocyte of the secondary subculture, a cell suspension was prepared to have cell concentration of 2.0×10$^5$ cells/ml in the same order as the step (4) for isolating and purifying the components having an astrocyte proliferative activity. D-MEM (10% FBS) was used as a medium. The prepared cell suspension of culture astrocyte was seeded at 100 μl/well to a 96 well microplate (Tissue Culture Treated Polystyrene/IWAKI) for cell culture by using a multi pipette (Eppendorf), and incubated under conditions of 37° C., 5.0% CO$_2$. 24 Hours later, to suppress cell proliferation of the astrocyte, the medium inside the well was replaced with D-MEM (0% FBS). After another 24 hours, the medium inside the well was replaced with D-MEM (0% FBS) in which various samples are dissolved in advance, and the astrocyte was exposed to the sample for 24 hours. In that case, D-MEM (0% FBS) not added with any sample was used as a control group. After the exposure to sample, by using a cell proliferation ELISA, BrdU chromogenic kit (Roche), operations based on the protocol of kit were performed. For measurement of an absorbance, a test for comparing proliferation accelerating activity was carried out using a microplate reader (Multi-Detection Microplate Reader/DAINIPPON SUMITOMO PHARMA). Incidentally, in the present test, the reaction time for BrdU labeling solution was set at 4 hours, the reaction time for POD labeled anti BrdU antibody reaction solution was set at 2 hours, and the reaction time for substrate solution was set at 30 minutes without using a solution for terminating the reaction. Furthermore, throughout the entire test, to prevent a loss of the cells in each order, tapping was not carried out and removal of a medium or a chemical reagent was carried out all by using a multi pipette.

[B] Results

Figure 6:
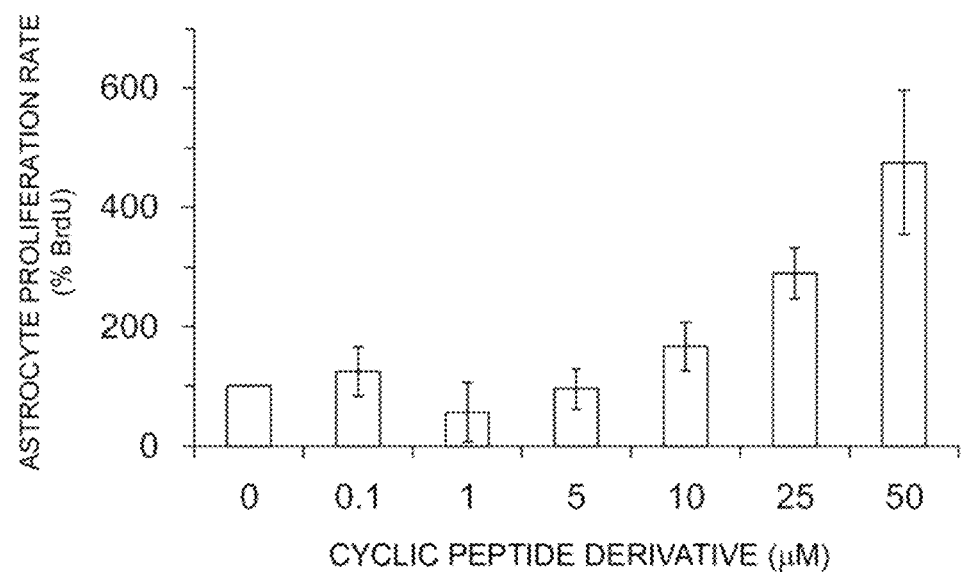
FIG. 6 is a graph illustrating the concentration dependency of the astrocyte proliferative activity of a cyclic peptide derivative.

As shown in FIG. 6, as a result of modifying the addition concentration of the cyclic peptide derivative to 0.1, 1, 5, 10, 25, and 50 μM, the astrocyte proliferation accelerating activity was observed with concentration dependency.

2. Comparative Test with Existing Pharmaceuticals in Terms of Astrocyte Proliferative Activity Zonisamide, which was used as a positive control, has been used as a therapeutic agent for Parkinson's disease. As one activity of zonisamide, the astrocyte proliferative activity was shown (Non Patent Literature 34). Accordingly, the astrocyte proliferative activity was compared between the cyclic peptide derivative and zonisamide. Furthermore, the astrocyte proliferative activity test was carried out for donepezil hydrochloride, eserin, and galantamine as a known therapeutic agent for cognitive disorder which has not been reported with any astrocyte proliferative activity until now, and comparison with the cyclic peptide derivative of the present invention was made.

[A] Methods

By using an astrocyte of the secondary subculture, an astrocyte proliferative activity test was carried out for a known pharmaceutical in the same order as the above 1. Astrocyte proliferation promoting activity test. Zonisamide (Wako) was prepared at 100 μM by dissolving it in MQ, and Aricept (registered trademark) (donepezil hydrochloride, abcam), eserin (SIGMA) and galantamine (abcam) were prepared at 25 μM by dissolving them in MQ to carry out the test.

[B] Results

Figure 7:
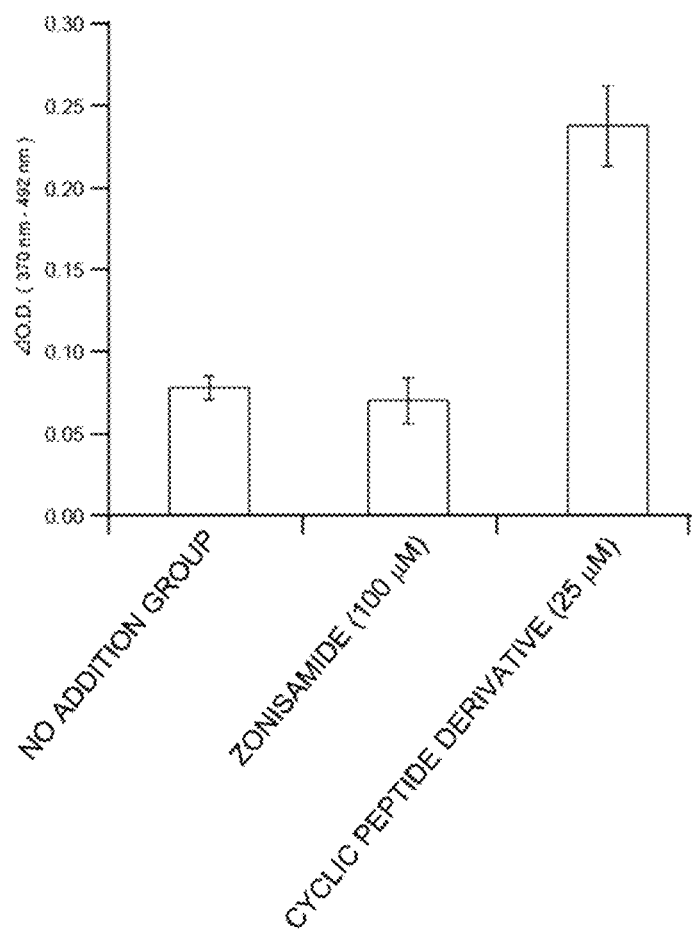
FIG. 7 is a drawing illustrating the astrocyte proliferative activity when the cyclic peptide derivative of the present invention or zonisamide is added to a cultured astrocyte.

As shown in FIG. 7, astrocyte proliferation was hardly observed from the control group and the group added with 100 μM zonisamide. On the other hand, from the group added with 25 μM of the cyclic peptide derivative, astrocyte proliferation which is about 12 times compared to the control group was confirmed. Based on this result, it was found that the astrocyte proliferative activity of the cyclic peptide derivative is more significant than the astrocyte proliferative activity of zonisamide.

Figure 8:
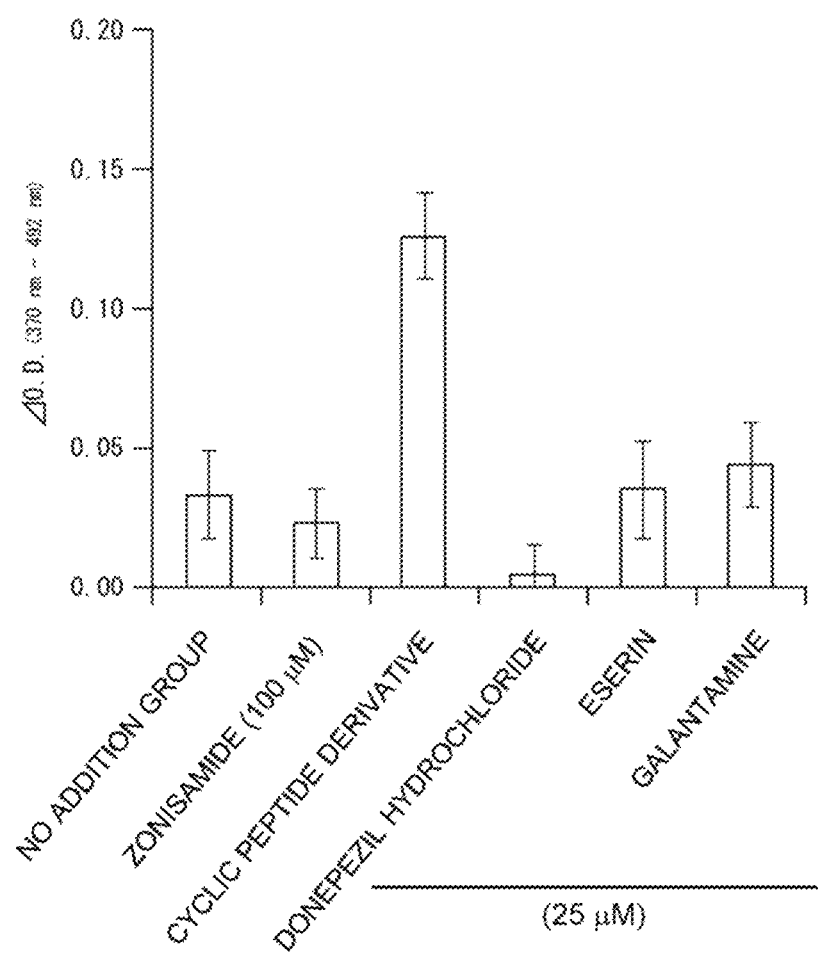
FIG. 8 is a drawing illustrating the astrocyte proliferative activity when the cyclic peptide derivative or a known pharmaceutical is added to a cultured astrocyte.
Figure 9:
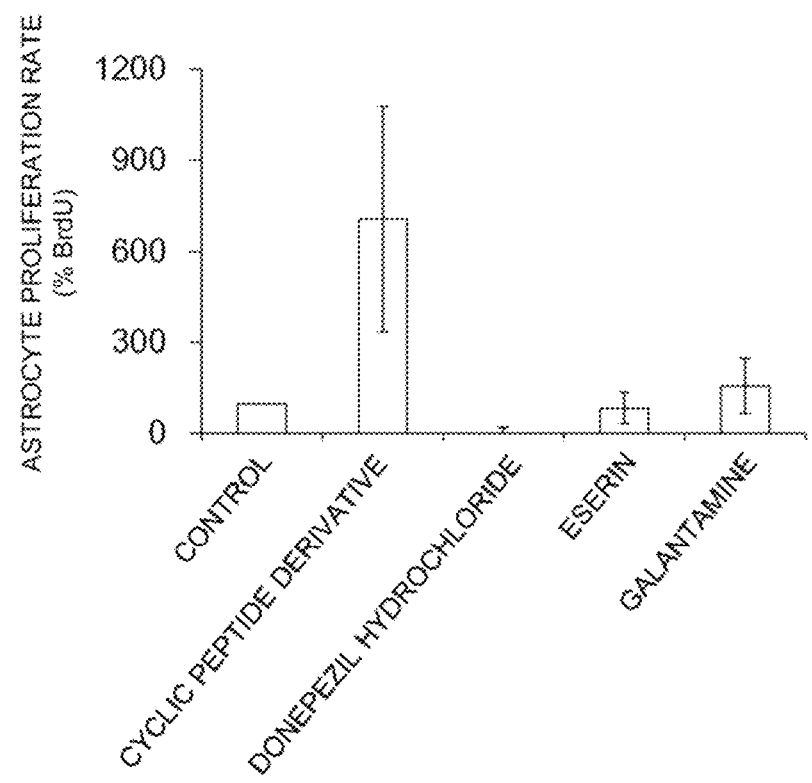
FIG. 9 is a drawing illustrating the astrocyte proliferative activity when the cyclic peptide derivative or a known pharmaceutical is added to a cultured astrocyte. On the vertical axis, concentration of BrdU which has been injected to an astrocyte is shown.

Furthermore, as shown in FIG. 8 and FIG. 9, because no significant astrocyte proliferative activity was observed even when donepezil hydrochloride, eserin, or galantamine as a therapeutic agent currently used in the clinic for treating Alzheimer's disease was added, it is believed that the conventional type therapeutic agent for Alzheimer's disease has absolutely no influence on the proliferation of astrocyte. In addition, it is believed that the astrocyte proliferative activity is an activity that is specific to the cyclic peptide derivative.

3. Test for Determining Astrocyte Specific Proliferation Activity by the Cyclic Peptide Derivative To see whether or not the astrocyte proliferation accelerating activity of the cyclic peptide derivative is a specific proliferative activity that is limited only to an astrocyte or it is based on a common cell proliferative activity, investigations were made by using normal human dermal fibroblasts (NHDF), human liver cancer cells (HepG2), and human leukemia cells (K562).

[A] Methods

The influence exhibited on proliferation of normal human dermal fibroblasts (NHDF), human liver cancer cells (HepG2), and human leukemia cells (K562) was measured in view of the method by Yang, et. al. (2007, Non Patent Literature 33). Seeding of each cell on a 96 well plate was carried out by adding 100 μl of a cell suspension in which normal human dermal fibroblasts are prepared at $2.5 \times 10^4$ cells/ml or human liver cancer cells and human leukemia cells are prepared at $5 \times 10^4$ cells/ml. Since the cyclic peptide derivative is added after dissolving it in PBS (−), only PBS (−) was added as a control.

[B] Results

Figure 10:
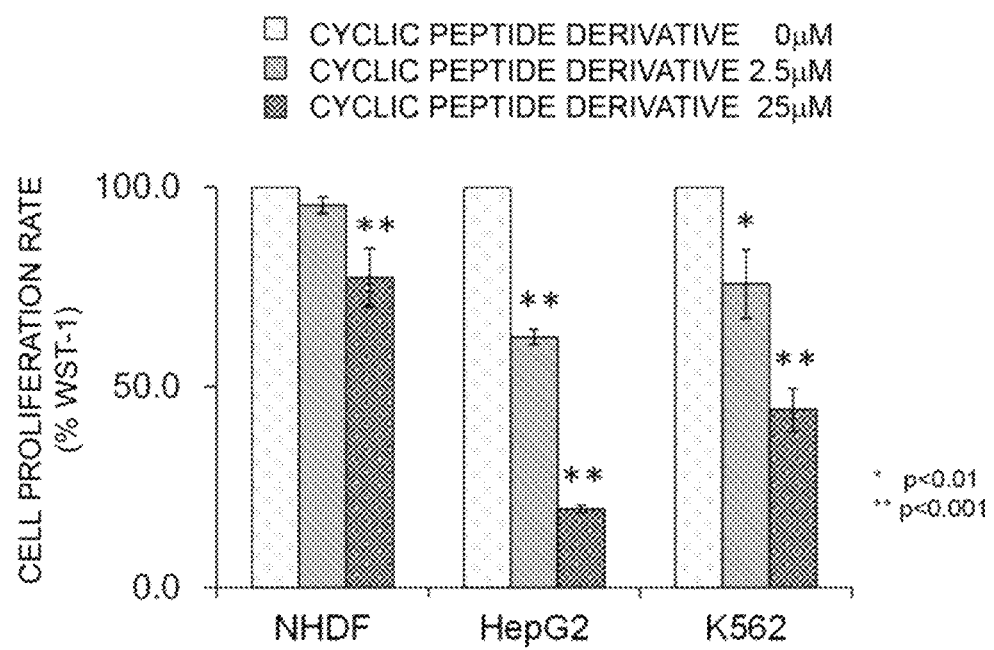
FIG. 10 is a drawing illustrating a cell proliferative activity when the cyclic peptide derivative is added to cultured normal human dermal fibroblasts (NHDF), human liver cancer cells (HepG2), or human leukemic cells (K562).

As shown in FIG. 10, at any concentration of 2.5 μM and 25 μM, a strong inhibitory activity on cell proliferation was observed by an addition of the cyclic peptide derivative. Meanwhile, in case of NHDF cells, the proliferation was inhibited in a significant sense by adding the cyclic peptide derivative of 25 μM compared to the group with no addition. However, as the cell proliferation rate was still maintained at 80% or so, it is believed that the cytotoxicity for normal cells is low. As such, it was found that the astrocyte proliferative action of the cyclic peptide derivative is not based on a common cell proliferative activity but based on the proliferative activity that is specific to an astrocyte.

<2> Acetylcholine Esterase Inhibitory Activity Test

Most of existing therapeutic agents for Alzheimer's disease have, as a target mechanism, the inhibitory activity for an acetylcholine esterase which is an enzyme for decomposing acetylcholine as a neurotransmitter. Namely, by inhibiting an acetylcholine esterase, the therapeutic agents for Alzheimer's disease increase an in vivo concentration of acetylcholine. Accordingly, determinations were made to compare the acetylcholine esterase (AChE) inhibitory activity of donepezil hydrochloride (Non Patent Literature 31) as a representative AChE inhibitor and the AChE inhibitory activity of the cyclic peptide derivative of the present invention.

[A] Methods

The inhibitory activity on acetylcholine esterase (AChE) was measured in view of the method by Nair, et. al. (Non Patent Literature 31), and concentration of donepezil hydrochloride (abcam) which has been used for comparative purpose was determined with reference to Sugimoto, et. al. (Non Patent Literature 32).

[B] Results

Figure 11:
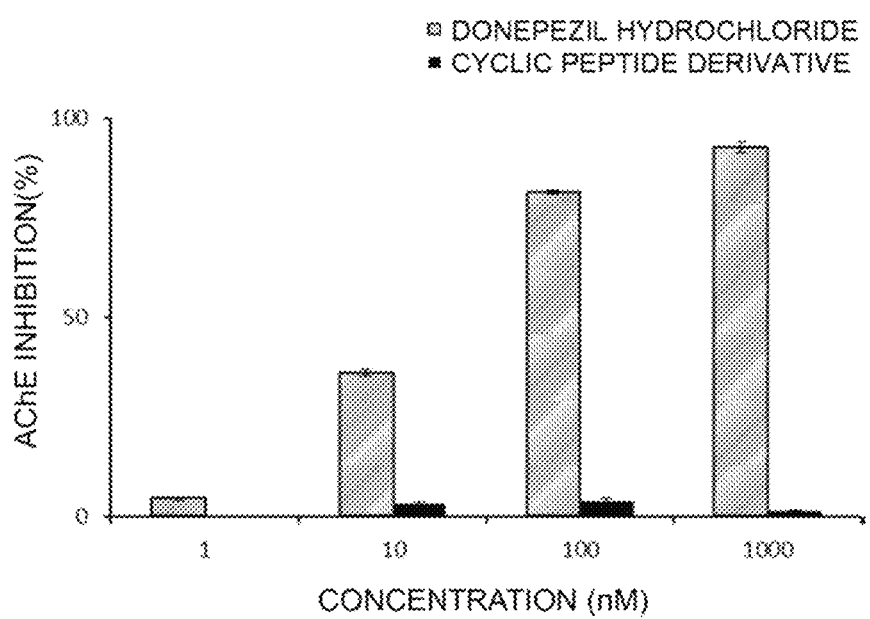
FIG. 11 is a drawing illustrating the acetylcholine esterase (AChE) inhibition activity when addition of the cyclic peptide derivative or donepezil hydrochloride is made.

As shown in FIG. 11, AChE inhibitory activity of 40% or so was observed with 10 nM donepezil hydrochloride. However, absolutely no AChE activity was observed with the cyclic peptide derivative having a concentration of 1000 nM.

Based on the results, it was confirmed that the donepezil hydrochloride as an existing therapeutic agent for Alzheimer's disease has an AChE inhibitory activity but has no astrocyte proliferative activity. On the other hand, it was confirmed that the cyclic peptide derivative of the present invention has an astrocyte proliferative activity but has no AChE inhibitory activity. Accordingly, it is considered that there is no common working mechanism between the working mechanisms of astrocyte proliferation and AChE inhibition, and the cyclic peptide derivative exhibits a specific activity of proliferating an astrocyte.

<3> Analysis of Astrocyte Gene Expression Activating Activity by Addition of the Cyclic Peptide Derivative By adding the cyclic peptide derivative of 25 µM to an astrocyte of the secondary subculture, the influence on expression of the gene of NGF, GDNF, VFGF-A, BDNF, and VGF as a representative neurotrophic factor was determined over time.

[A] Methods

Except that a cell suspension of an astrocyte of the secondary subculture was prepared to have cell concentration of $3\times10^5$ cells/ml and the time for exposing the astrocyte to the above 25 µM cyclic peptide derivative was set at 0, 1, 2, 4, 8, 12, and 24 hours, the astrocyte was cultured in the same order as above <6>. As a control group, LG-D-MEM (0% FBS) not added with any cyclic peptide derivative was used.

Each astrocyte which has been exposed to the cyclic peptide derivative during each time described above was collected, and then, by using RNeasy Mini Kit (QIAGEN), extraction and purification of total RNA were carried out. The extracted total RNA was quantified by using Nano Photometer (IMPLEN). For the reverse transcription reaction, cDNA was synthesized by reacting 500 ng of total RNA with PrimeScript RT Master Mix (TaKaRa) at 37° C. for 15 minutes using GeneAmp PCR System 9600 (PERKIN ELMER), and the reaction was terminated by heating for 5 seconds at 85° C.

By having the synthesized cDNA as a template and using each of various commercially available primers (TaKaRa) that are described in Table 6, an expression analysis was carried out with SYBR premix Ex Taql (TaKaRa) and a real time PCR device, Thermal Cycler Dice TP800 (TaKaRa).

TABLE 6

| Gene name | Nucleotide sequence of primer | SEQ ID NO: |
|---|---|---|
| NGF | F: TGCCAAGGACGCAGCTTTC | 1 |
|  | R: TGAAGTTTAGTCCAGTGGGCTTCAG | 2 |
| GDNF | F: TCAGCTGCCCAGCACATTTC | 3 |
|  | R: TGGGAGCATCAGCTACCACATC | 4 |
| VEGF-A | F: ACATTGGCTCACTTCCAGAAACAC | 5 |
|  | R: TGGTTGGAACCGGCATCTTTA | 6 |
| BDNF | F: GCCGTTTACCAAATTAACCTTTGTC | 7 |
|  | R: CCACACAATTGCTGATGTCTCC | 8 |
| VGF | F: CCAGACGGGAAAGGCTGTTCTAT | 9 |
|  | R: GGAGAAGTGGGTAAGTTCACAGCAA | 10 |
| GAPDH | F: GTC TCC TCT GACTTC AACA | 11 |
|  | R: CAG GAA ATG AGC TTG ACA AA | 12 |

As for the specific commercially available primers that are described in Table 6, the followings were used. As a primer for NGF gene, Mus musculus nerve growth factor (Ngf), transcript variant 1, and mRNA (MA075785, TaKaRa) were used. As a primer for GDNF gene, Mus musculus glial cell line derived neurotrophic factor (Gdnf) and mRNA (MA102345, TaKaRa) were used. As a primer for VEGF-A gene, Mus musculus vascular endothelial growth factor (Vegfa), transcript variant 1, and mRNA (MA128545, TaKaRa) were used. As a primer for BDNF gene, Mus musculus brain derived neurotrophic factor (Bdnf), transcript variant 2, and mRNA (MA138332, TaKaRa) were used. As a primer for VGF gene, Mus musculus VGF nerve growth factor inducible (Vgf) and mRNA (MA157656, TaKaRa) were used.

Expression level of each target gene was compared after calibration by using, as an internal standard, GAPDH as one of the housekeeping genes.

[B] Results

Figure 12:
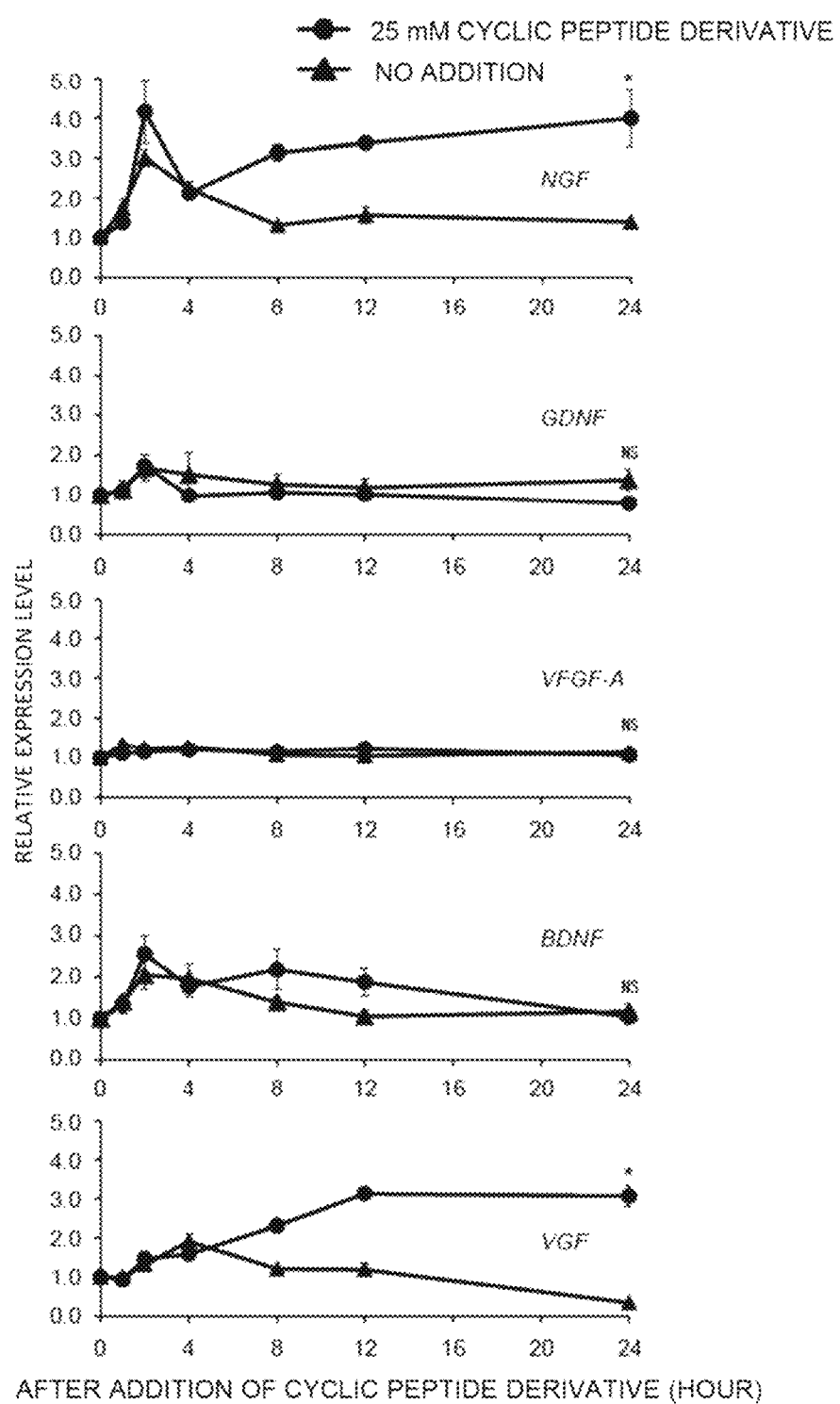
FIG. 12 is a graph illustrating the result of an analysis of a neurotropic factor-related gene expression in cultured astrocyte added with the cyclic peptide derivative. The quantification was also made for GAPDH gene of which expression is considered to be constant in the cells of any treatment group (i.e., housekeeping gene, internal standard), and the quantification result of a target gene for determination was calibrated based on the quantification of GAPDH gene. The lower part indicates the expression amount of a gene in culture astrocyte which has not been added with anything. The upper part indicates the expression amount of a gene in culture astrocyte after the addition of the cyclic peptide derivative.

According to the results, expression of the genes of NGF and VGF increased from 8 hours to 24 hours after the addition of the cyclic peptide derivative as shown in FIG. 12, and compared to the result before the addition of the cyclic peptide derivative, a statistically significant difference ($p<0.05$) was observed.

It is known that, when Ropinirole which is one of therapeutic agents for Parkinson's disease and a dopamine agonist is administered to an astrocyte of mouse, genes of neurotrophic factor NGF, GDNF, and BDNF are activated (Non Patent Literature 35). Furthermore, ifenprodil known as an antagonist for an N-methyl-D-aspartate (NMDA) receptor is used as an agent to improve dizziness accompanying a sequelae of cerebral infarction or a sequelae of cerebral hemorrhage. Activation of NGF, BDNF, and GDNF genes in mouse astrocyte and protein production of each of them by ifenprodil have been confirmed (Non Patent Literature 36). Furthermore, it is known that serotonin as an anti-depressant activates VGF to enhance the synapse activity in a hippocampus neuron, and promotes neurogenesis in a hippocampal dentate gyrus (Non Patent Literature 37).

Accordingly, as the cyclic peptide derivative induces an activation of NGF and VGF genes in an astrocyte, it can be applied as a therapeutic agent for various brain function-related diseases, including a therapeutic agent for dizziness•anti-psychotic drug related with Parkinson's disease•brain dysfunction disorder.

<4> Test for Learning Memory Improvement in Senescence-Accelerated Model Mouse by Oral Administration of the Cyclic Peptide Derivative 1) Mouse As a mouse for an in vivo test of the cyclic peptide derivative, senescence-accelerated model mouse SAMP8 which is used as a cognitive disorder model animal of initial Alzheimer's disease accompanied with aging was selected, and as a control, SAMR1 mouse with normal aging was selected.

19-Week old male mice of SAMR1 and SAMP8 were purchased from Japan SLC, Inc., and divided into 5 groups, i.e., mouse group with normal aging (SAMR1), senescence-accelerated model mouse group (SAMP8), {P8+donepezil hydrochloride 1250 µg/kg/day} group as a positive control, and {P8+cyclic peptide derivative 2.5 µg/kg/day} group and {P8+cyclic peptide derivative 25 µg/kg/day} group as a test group. The animal was individually kept, i.e., one animal per cage, in a room with controlled environment {room temperature: 23±2° C., light and dark cycle: lighting time of 12 hours (time with light: 07:00 to 19:00), time without light: 12 hours}. The test was carried out in a time window of from 13:00 to 18:00 in an incubator with constant temperature and constant humidity (temperature 23±2° C., humidity 50±10%). After 10 days of an acclimation period, all mice were provided with standard meal (MEQ, Oriental Yeast Company) and body weight of the animal was recorded everyday during the entire test period. Water, feeds, and excretion amount (i.e., weight of flooring) were weighed 2 times per week. Identification of an individual mouse was carried out based on the cage number. The present study follows the law of humane treatment of animals and the guidelines for care and use of a test animal, and the study was conducted under an authorization of Animal Test Committee of Iwate University.

2) Oral Administration of the Cyclic Peptide and Pharmaceuticals to Mouse

For the mice divided into the 5 groups described above, the following treatments were carried out.

(1) Mouse with normal aging group: By using a gastric sonde, 0.9% physiological saline was administered for 5 weeks.

(2) Senescence-accelerated model mouse group: By using a gastric sonde, 0.9% physiological saline was administered for 5 weeks. Incidentally, the oral administration was continued until the whole behavior test is over, and the oral administration was carried out for 8 weeks in total.

(3) {P8+donepezil hydrochloride 1250 μg/kg/day} group: As a positive control, donepezil hydrochloride (Sanyo Chemical Laboratories CO., LTD.) was dissolved in MQ and prepared to have a concentration of 1250 μg/kg (bodyweight), and then orally administered to a SAMP8 for 5 weeks by using a gastric sonde. The concentration was accurately calculated based on the bodyweight which has been measured every day. Incidentally, the oral administration was continued until the whole behavior test is over, and the oral administration was carried out for 8 weeks in total.

(4) {P8+cyclic peptide derivative 2.5 μg/kg/day} group: As a test group, the cyclic peptide derivative was dissolved in MQ and prepared to have a concentration of 2.5 μg/kg (bodyweight), and then orally administered to a SAMP8 for 5 weeks by using a gastric sonde. The concentration was accurately calculated based on the bodyweight which has been measured every day. Incidentally, the oral administration was continued until the whole behavior test is over, and the oral administration was carried out for 8 weeks in total.

(5) {P8+cyclic peptide derivative 25 μg/kg/day} group: As a test group, the cyclic peptide derivative was dissolved in MQ and prepared to have a concentration of 25 μg/kg (bodyweight) (Non Patent Literature 39), and then orally administered to a SAMP8 for 5 weeks by using a gastric sonde. The concentration was accurately calculated based on the bodyweight which has been measured every day. Incidentally, the oral administration was continued until the whole behavior test is over, and the oral administration was carried out for 8 weeks in total.

Furthermore, the every mouse of the 5 groups was provided with a standard meal and water until the whole behavior test is over.

3) Step Through Passive Avoidance Test (1) Apparatus

The apparatus (manufactured by O'HARA & CO., LTD.) consists of a light room and a dark room with inverse-trapezoidal shape (light room: top surface 100×130 mm, bottom surface 42×130 mm, height 90 mm, dark room: top surface 100×160 mm, bottom surface 42×160 mm, height 90 mm). On the bottom of both rooms, stainless bars with diameter of 2.0 mm were arranged with an interval of 6.0 mm, and only the bottom surface of the dark room can be electrically charged. The two rooms were blocked by a partition plate which can be freely open and closed in vertical direction by a person who performs the test. For an acquisition trial, after adding a mouse in a light room illuminated with a white fluorescent light (15 W, 400 lux), the test was initiated by opening the partition plate. Furthermore, on the left and right sides of the entrance of a dark room, an infrared (IR) sensor for detecting an entry of a mouse was provided, and the signal detected by this IR sensor was used for measurement of entry time or as a trigger for generating an electric shock.

(2) Order

The order of the step through passive avoidance test was based on the description of Tsushima et. al. (Non Patent Literature 38). For the purpose of selecting an abnormal mouse before the main test, a pre-acquisition trial was carried out. For the pre-acquisition trial, a mouse was placed in a light room while the partition door was left open, and the time until the entry into a dark room was measured. The step through passive avoidance test utilizes the minus running habit of a mouse, i.e., mouse prefers a dark place over a light place. For such reasons, if the mouse placed in a light room appears to stay for 60 seconds or longer in a light room in the pre-acquisition trial, the animal was found to be an abnormal animal, and thus not used for the following test.

On the $1^{st}$ day of the test, a pre-acquisition trial was performed followed by an acquisition trial. For the acquisition trial, a mouse was placed in a light room while the partition door is closed, and 30 seconds later, the partition door was open and the time until the mouse enters a dark room (i.e., latency) was measured. At the time point at which the rear paw of a mouse enters the dark room or a reaction with an IR sensor in the dark room is shown, the partition door was closed, and 2 seconds after the mouse has entered the dark room, an electric shock of 0.3 mA was applied for 4 seconds.

On the $2^{nd}$ day of the test, a post-shock trial was performed (i.e., 24 hours after the acquisition trial). For the post-shock trial, the same operations as the acquisition trial were carried out except that, unlike the acquisition trial, the electric shock was not applied. The latency was measured with a maximum of 300 seconds.

(3) Results

Figure 13:
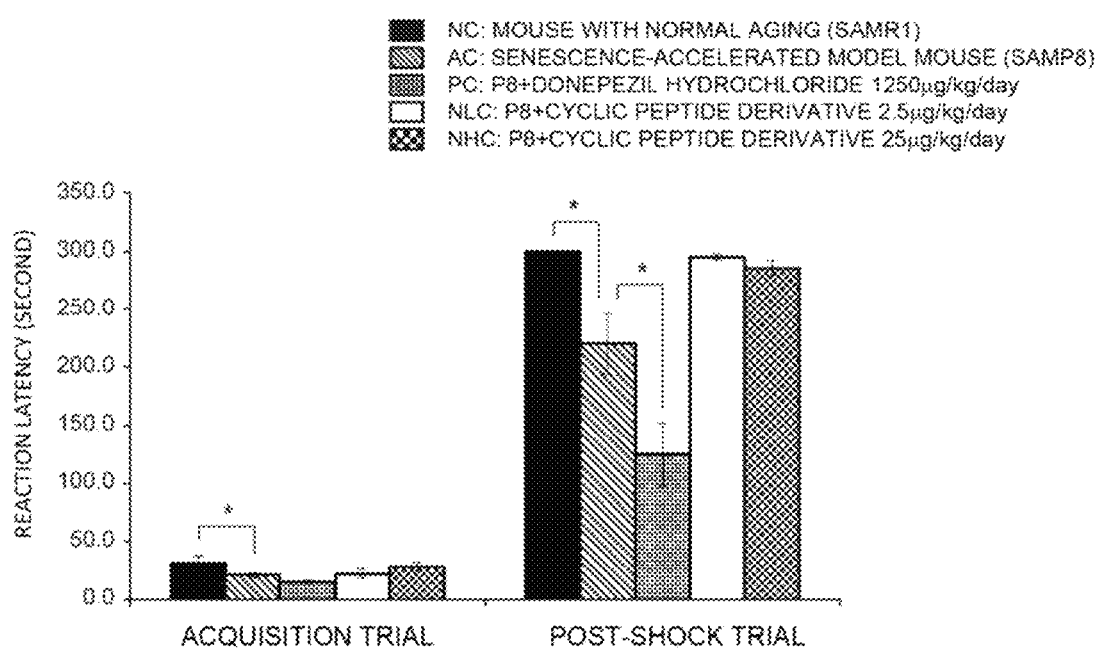
FIG. 13 is a graph illustrating the result of a step-through passive avoidance test for a mouse with normal aging and a senescence accelerated model mouse, both administered with the cyclic peptide derivative.

As shown in FIG. 13, when the mouse with normal aging (SAMR1) and the senescence-accelerated model mouse (SAMP8) are compared to each other in terms of latency in post-shock trial of the passive avoidance test, the senescence-accelerated model mouse has a short latency in significant sense, showing a low contextual learning ability ($p<0.05$). Furthermore, when the senescence-accelerated model mouse which has not been administered with anything and the senescence-accelerated model mouse which has been administered with donepezil hydrochloride are compared to each other in terms of latency, the senescence-accelerated model mouse which has been administered with donepezil hydrochloride has a short latency in significant sense compared to the senescence-accelerated model mouse which has not been administered with anything, showing a low contextual learning ability ($p<0.05$). Incidentally, it was confirmed that, in the senescence-accelerated model mouse which has been administered with 2.5 μg/kg/day or 25 μg/kg/day of the cyclic peptide derivative, the contextual learning ability was recovered to the level of a mouse with normal aging.

From the above, it was confirmed that, according to oral administration of the cyclic peptide derivative of the present invention to a senescence-accelerated model mouse, the contextual learning ability is clearly improved more compared to donepezil hydrochloride as a known therapeutic agent for cognitive disorder.

4) Morris Water Maze Test (1) Apparatus and Setting of Apparatus

The apparatus (manufactured by O'HARA & CO., LTD.) and a setting of the apparatus are as described below. First, a cylindrical pool (diameter of 100 cm and depth of 30 cm) was set 80 cm above the bottom. Subsequently, water was added to the pool to have depth of 20 cm (water temperature of 25±1° C.) and a transparent platform (diameter of 10 cm and height of 19 cm) was set such that it is immersed 1 cm below the water surface. Subsequently, water of the pool was clouded with a commercially available white poster color so that the platform remains invisible to a mouse in swimming. After installing a black CCD camera at a position which is 100 cm right above the water surface at approximately the center of the pool, a photographic image covering every quadrant was automatically taken and automatically recorded by using the black CCD camera. As the camera is connected to a computer, the swimming path of a mouse was stored in the computer at an interval of 0.5 second. For the recording of swimming path and analysis of image, Image WMH 2.08 and Image WM 2.12 (manufactured by O'HARA & CO., LTD) which are a software based on the NIH Image developed and published by NIH (The U.S. National Institute of Health) were used.

(2) Order

The order of the Morris water maze test was based on the method of Tsushima et. al. (Non Patent Literature 38). The test was initiated at the same time of everyday for 9 days. On the $1^{st}$ day, each mouse was allowed to swim once for 1 minute so that the mouse becomes familiar with the pool. After that, by setting a label with height of 10 cm on the platform, the mouse was allowed to recognize the presence of platform. Furthermore, at the time of introducing a mouse to the pool, the mouse was allowed to enter water, from the mouse introduction point designated by the computer, in wall direction of the pool, and the person conducting the test rapidly disappeared to a location that is not seen by a mouse. When the mouse reaches the platform within 60 seconds, the mouse was kept for 15 seconds on the platform, and then retrieved. When the mouse could not reach the platform by swimming within 60 seconds, the mouse was transferred to the top of the platform by the hands of a person running the test, and after keeping it for 15 seconds on the platform, the mouse was retrieved.

On the $2^{nd}$ to $8^{th}$ day, a training allowing the mouse to memorize the location of platform was carried out. The training was continuously carried out 4 times per day for single mouse. As for the method for training, the same operation as that of the $1^{st}$ day was carried out, and the time for reaching the platform was recorded. Incidentally, in a case in which the mouse cannot reach the platform after swimming for 60 seconds, the mouse was transferred to the top of the platform by the hands of a person running the test, and after keeping it for 15 seconds on the platform, the reaching time of 60 seconds was recorded.

On the $9^{th}$ day, a probe test was carried out. For the probe test, the platform was removed from the pool, and after allowing the mouse to swim for 60 seconds, the visit rate (i.e., visit time) in each domain of each quadrant (¼ circle of circular pool) was measured. Incidentally, the probe test was carried out once for each mouse.

(3) Results

Figure 14:
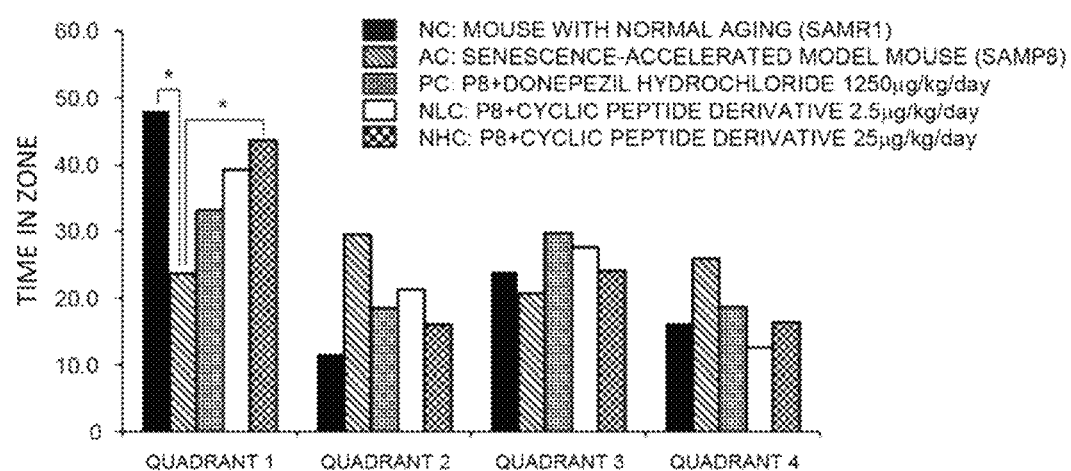
FIG. 14 is a graph illustrating the result of a Morris water maze test for a mouse with normal aging and a senescence accelerated model mouse, both administered with the cyclic peptide derivative.

As shown in FIG. 14, from the values of the mouse time in zone (%) on the $2^{nd}$ to the $8^{th}$ day of the test in quadrant 1 provided with a platform, it was confirmed that the spatial learning ability is significantly recovered according to an administration of the cyclic peptide derivative of the present invention. Namely, when comparison is made between the mouse with normal aging and the senescence-accelerated model mouse, the value of the mouse time in zone (%) in quadrant 1 was significantly low in the senescence-accelerated model mouse ($p<0.05$). Incidentally, when comparison is made between the senescence-accelerated model mouse and the senescence-accelerated model mouse administered with the cyclic peptide derivative at 25 µg/kg/day, it was found that the spatial learning ability is significantly recovered in the senescence-accelerated model mouse which has been administered with the cyclic peptide derivative at 25 µg/kg/day ($p<0.05$).

Based on the above, it was confirmed that, according to an oral administration of the cyclic peptide derivative to a senescence-accelerated model mouse, the spatial learning ability is more clearly improved compared to donepezil hydrochloride as a known therapeutic agent for cognitive disorder.

<5> Hair Anti-Aging Effect on Senescence-Accelerated Model Mouse by Oral Administration of the Cyclic Peptide Derivative As a neuron protective activity of an astrocyte, a multifunctional property including energy supply to a neuronal cell, forming of blood brain barrier (BBB), ability of absorbing stimulatory amino acids, anti-oxidizing defense, or dedifferentiation into a neural stem cell is known (Non Patent Literatures 35 and 36).

Accordingly, in addition to the improvement of cognitive function and improvement of learning memory ability, proliferation of an astrocyte caused by the cyclic peptide derivative is expected to have a multifunctional property of the effect in an in vivo test. In particular, because it is known that neurogenesis from a skin dermal stem cell can be induced by a signal derived from an astrocyte (Non Patent Literature 37), an interaction between an astrocyte and a dermal stem cell as mediated by a molecular signal is expected.

Considering that the anti-aging effect for body hair and hair has been analyzed until now by using a senescence-accelerated model mouse (SAMP8) (Non Patent Literature 40), the inventors of the present invention also conducted an analysis regarding the anti-aging effect for body hair and hair for a senescence-accelerated model mouse administered with the cyclic peptide derivative by using a static and dynamic friction tester and a scanning probe microscope (SPM).

1) Coefficient of Friction Measurement Test

Coefficient of friction of animal hair and body hair is closely related to the state of cuticle as a scale-like tissue present on a surface of hair and body hair, and it is considered that the value of coefficient of friction (COF) increases as damages on cuticle of a hair and body hair increases (Non Patent Literature 40). It is also known that, when the damages on cuticle are high, moisture or nutrients of hair and body hair are lost from the damaged part of cuticle.

(1) Apparatus

As for the apparatus, a handy rub tester TL701 (manufactured by Trinity-Lab Inc.), which is a static and dynamic friction tester, was used. For the measurement, this apparatus does not require cutting of any human or animal hair and body hair to have a measurement sample, and it is a static and dynamic friction tester which allows direct measurement of a state in which hair and body hair grows from a skin. Namely, the apparatus even allows measurement of friction on a surface of skin or materials which have a complex curved surface.

(2) Methods

The contact member of a static and dynamic friction tester was closely pressed on body hair on forehead part of a mouse, and while applying a load of about 1 N, the member was moved, through an area between two ears, from the forehead to neck part of the mouse for about ten seconds, and the coefficient of friction (COF) was measured. The coefficient of friction (COF) was measured 5 to 10 times per mouse, and an average value thereof was calculated.

2) Test for Observing Body Hair of Senescent Mouse Using Scanning Probe Microscope (1) Apparatus As for the apparatus, tapping mode scanning probe microscope (SPM: SPA400, Hitachi High-Tech Science Corporation) was used.

(2) Methods

As a sample, body hair in head and neck part of a mouse was collected by plucking from the origin, and the observation was made by using the tapping mode scanning probe microscope described above.

3) Results

Figure 15:
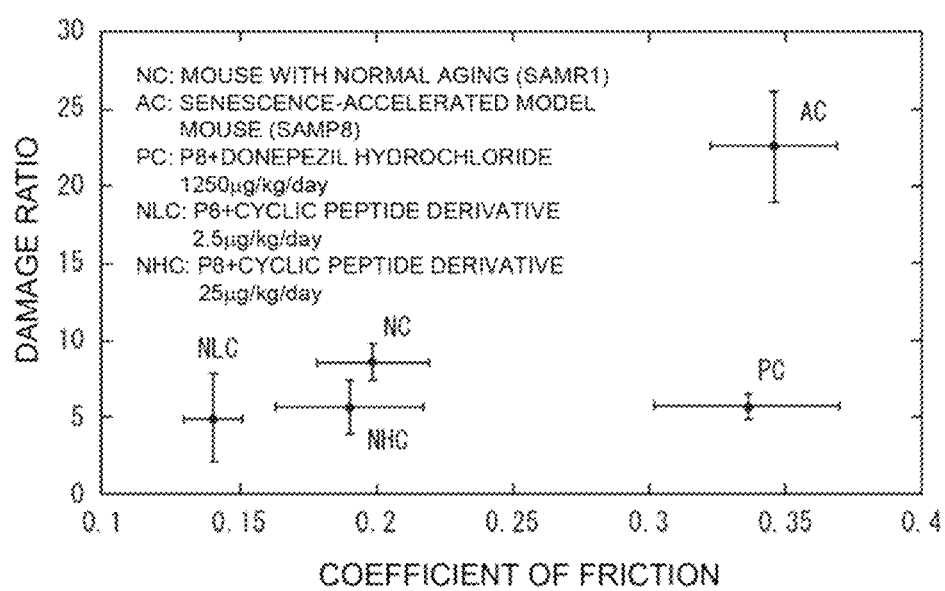
FIG. 15 is a graph illustrating the Coefficient of friction and a damaged area ratio of a body hair of a mouse with normal aging and a senescence accelerated model mouse, both administered with the cyclic peptide derivative.

As shown in FIG. 15, the coefficient of friction (COF) of a mouse which has been measured by using a static and dynamic friction tester was plotted against an X axis, and the damaged area ratio on a surface of mouse body hair which has been measured by using SPM was plotted against a Y axis. Then, the correlative relationship between them was evaluated. The body hair from a senescence-accelerated model mouse exhibited high numerical values of coefficient of friction (COF) and damage ratio, and both of those two indicators were low in a mouse with normal aging. Based on this result, it is considered that, as one characteristic of a senescence-accelerated model mouse, aging of body hair is yielded and quality of hair is also deteriorated. Meanwhile, in a senescence-accelerated model mouse which has been orally administered with donepezil hydrochloride as a known therapeutic agent for cognitive disorder, the damage ratio on a surface of mouse body hair was at the same level as that of the mouse with normal aging. However, the coefficient of fraction on a mouse body hair is the same level as that of the senescence-accelerated model mouse, and thus a significant recovery was not observed.

On the other hand, when a senescence-accelerated model mouse is orally administered with the cyclic peptide derivative at 2.5 µg/kg/day or 25 µg/kg/day, both the coefficient of friction (COF) and damage ratio on a surface of mouse body hair were lowered to the same level as those of a mouse with normal aging, and thus the hair quality was found to be improved.

Based on the above, it is considered that the cyclic peptide derivative of the present invention has a possibility of exhibiting even an anti-aging effect on hair.

<6> Comparison of Astrocyte Proliferative Activity in *Paecilomyces tenuipes* from Silkworm, Other Plant Worms, or Pupae of Silkworm Itself Used as a Medium With regard to *Cordyceps sinennsis* from Tibet as representative plant worms, many physiologically active substances were identified (Non Patent Literatures 1 and 2). Furthermore, *Paecilomyces tenuipes* from silkworm is commercially available in Korea and China. However, as there is no finding regarding an astrocyte proliferative activity, herein comparison is made again.

1) Materials

As a material for comparison, 4 samples including dry powder of *Cordyceps sinennsis* from Tibet, tank culture dry powder of *Cordyceps sinennsis* from Tibet, dry powder of *Paecilomyces tenuipes* from silkworm from Korea, and dried pupae of silkworm as medium, and 2 samples including *Paecilomyces tenuipes* from silkworm which contains the cyclic peptide derivative of the present invention (*Paecilomyces tenuipes* from silkworm which has been cultured by using dried pupae of silkworm as hosts and *Paecilomyces tenuipes* from silkworm which has been cultured by using raw pupae of silkworm as hosts), i.e., 6 samples were used in total.

2) Methods

For the above 6 samples, according to hot water extraction of the step (1) in the isolation and purification step for the cyclic peptide derivative of the present invention shown in FIG. 2, a hot water extract MQ layer was obtained. Subsequently, the obtained hot water extract MQ layer was eluted into 7 fractions (F1 to F7) by the reverse phase flash column chromatography of the step (2). For all of those obtained 7 fractions, an astrocyte proliferative activity test was carried out at a concentration of 100 µg/ml, and the physiological activity for those fractions were compared to each other.

3) Results

Figure 16:
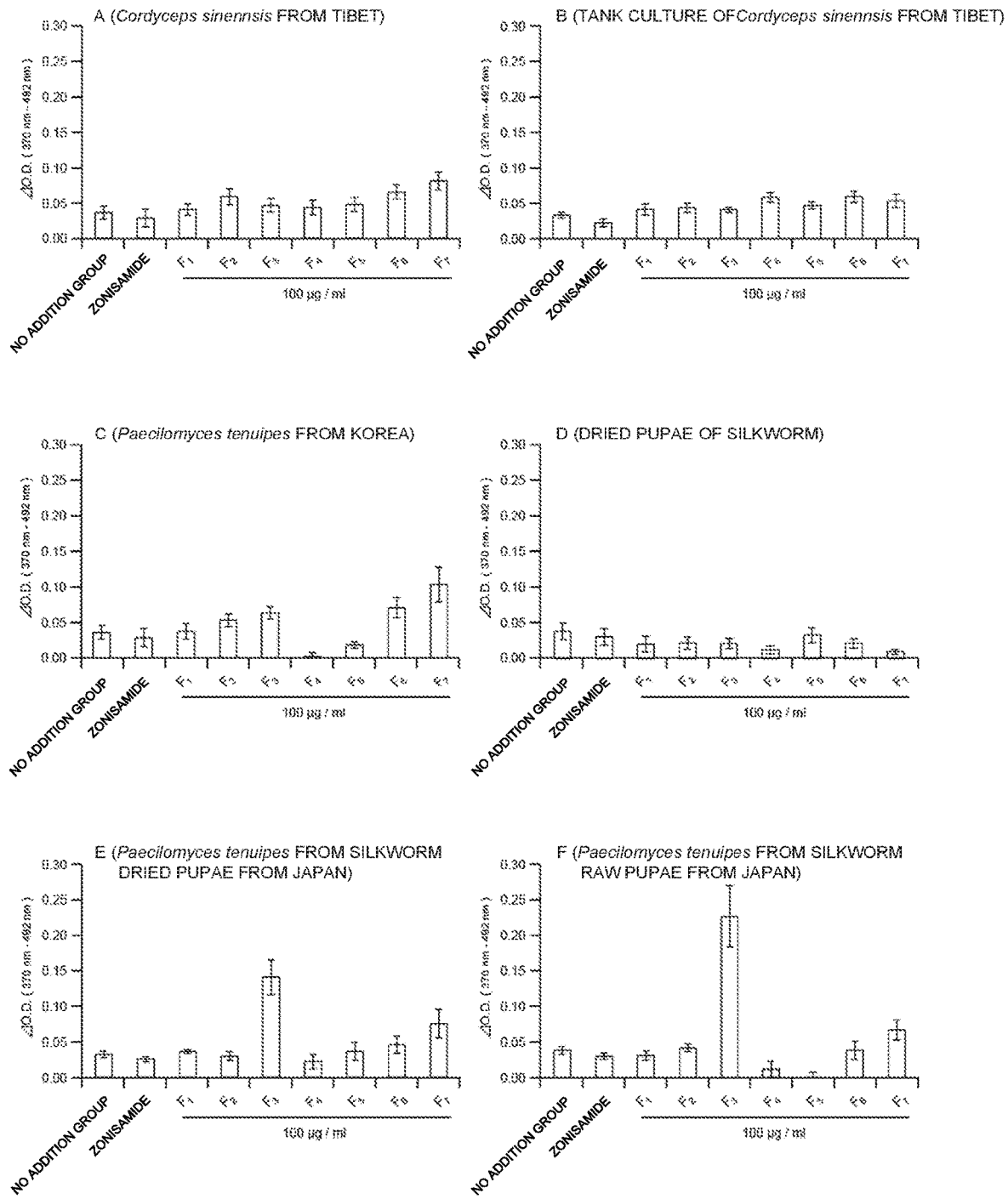
FIG. 16 includes graphs A to F illustrating the result of the astrocyte proliferative activity of an extract of the plant worms and silkworm pupae as hosts, each being different in terms of region of production, type, and culture method.

As shown in graphs E and F of FIG. 16, except the significant activity of F3 of *Paecilomyces tenuipes* from silkworm from Japan, F7 of *Paecilomyces tenuipes* from Korea exhibited a slight activity in graph C of FIG. 16 but all fractions of any plant worms in graphs A, B and D of FIG. 16 were hardly observed with any astrocyte proliferative activity, and thus it was found that the cyclic peptide derivative is absent therein, and even when it is acknowledged to be present, it is present at a level of trace amount. Furthermore, because the activity was not observed from the dried pupa of silkworm only which becomes a medium, it is believed that the cyclic peptide derivative was synthesized as a metabolic product of *Paecilomyces tenuipes* which is parasitic on pupae of silkworm. Accordingly, it was confirmed that use of pupae of silkworm as hosts for *Paecilomyces tenuipes* are desirable for production of the cyclic peptide derivative.

Incidentally, it is considered that *Paecilomyces tenuipes* produced by tank culture can also increase the content of pupae of silkworm powder in culture, thus enabling obtainment of the cyclic peptide derivative.

CITATION LIST

Patent Literature

Patent Literature 1: JP 2003-252876 A
Patent Literature 2: JP 2012-56867 A
Patent Literature 3: JP 2013-184923 A Non Patent Literature Non Patent Literature 1: Paterson, R. R. M. (2008) *Cordyceps*—A traditional Chinese medicine and another fungal therapeutic biofactory Phytochemistry, 69, 1469-1495.
Non Patent Literature 2: Yamaguchi, Y., Kagota, S., Nakamura, K., Shinozuka, K. and Kunimoto, M. (2000) Antioxidant activity of the extracts from fruiting bodies of cultured *Cordyceps sinensis*. Phytother. Res., 14, 647-649.
Non Patent Literature 3: Kuo, Y. C., Tsai, W. J., Wang, J. Y., Chang, S. C., Lin, C. Y. and Shiao, M. S. (2001) Regulation of bronchoalveolar lavage fluids cell function by the immunomodulatory agents from *Cordyceps sinensis*. Life Sciences, 68, 1067-1082.
Non Patent Literature 4: Choi, S. B., Park, C. H., Choi, M. K., Jun, D. W. and Park, S. (2004) Improvement of insulin resistance and insulin secretion by water extracts of *Cordyceps militaris, Phellinus linteus*, and *Paecilomyces tenuipes* in 90% pancreatectomized rats. Biosci. Biotechnol. Biochem. 68, 2257-2264.

Non Patent Literature 5: Koh, J.-H., Kim, J.-M., Chang, U.-J. and Suh, H.-J. (2003) Hypocholesterolemic effect of hot-water extract from mycelia of *Cordyceps sinensis*. Biol. Pharm. Bull. 26, 84-87.

Non Patent Literature 6: Bok, J. W., Lermer, L., Chilton, J., Klingeman, H. G. and Neil Towers, G. H., (1999) Antitumor sterols from the mycelia of *Cordyceps sinensis*. Phytochemistry, 51, 891-898.

Non Patent Literature 7: Rao, Y. K., Fang, S. H. and Tzeng, Y. M. (2007) Evaluation of the anti-inflammatory and anti-proliferation tumoral cells activities of Antrodia camphorate, *Cordyceps sinensis*, and *Cinnamomum osmophloeum* bark extracts. J. Ethnopharmacology, 114, 78-85.

Non Patent Literature 8: Tuli H S, Sharma A K, Sandhu S S, Kashyap D. (2013) Cordycepin: a bioactive metabolite with therapeutic potential. Life Sci. 93, 863-869.

Non Patent Literature 9: Yue K, Ye M, Zhou Z, Sun W, Lin X. (2012) The genus Cordycepes: a chemical and pharmacological review. J. Pharm. Pharmacol. 65, 474-493.

Non Patent Literature 10: Isaka Masahiko (2007) Studies on Novel Bioactive Compounds from *Cordyceps*, Journal of Synthetic Chemistry, 65, 700-708.

Non Patent Literature 11: Fujita Junpei (2008) Function and structure analysis of physiologically active substances from silkworm *Cordyceps*. pp. 2-5, Master thesis, Iwate University Graduate School of Aricultural Sciences, MS Programs of Agricultural Life Science Non Patent Literature 12: Sakakura, A., Suzuki, K., Katsuzaki, H., Komiya, T. Imamura, T., Aizono, Y. and Imai, K. (2005) Hanasanagin: a new antioxidative pseudo-di-peptide, 3,4-diguanidinobutanoyl-DOPA, from the mushroom, *Isaria japonica*. Tetrahedron Letters, 46, 9057-9059.

Non Patent Literature 13: Sakakura, A., Shioya, K., Katsuzaki, H., Komiya, T., Imamura, T., Aizono, Y. and Imai, K. (2009) Isolation, structural elucidation and synthesis of a novel antioxidative pseudo-di-peptide, Hanasanagin, and its biogenetic precursor from the *Isaria japonica* mushroom. Tetrahedron, 65, 6822-6827.

Non Patent Literature 14: Le Roux P D, Esquenazi S: Astrocytes mediatecerebral cortical neuronal axon and dendrite growth, in part, by release of fibroblast growth factor. Neurol Res, 24: 81-92, 2002.

Non Patent Literature 15: Biran R, Noble M D, Tresco, P A: Directed nerve outgrowth is enhanced by engineered glial substrates. Exp Neurol, 184: 141-152, 2003.

Non Patent Literature 16: Slezak M, Pfieger F W: New roles for astrocytes: Regulation of CNS synaptogenesis. Trends Neurosci, 26: 531-535, 2003.

Non Patent Literature 17: Ullian E M, Christopherson K S, Barres B A: Role for glia in synaptogenesis. Glia, 47: 209-216, 2004.

Non Patent Literature 18: Schousboe A, Sarup A, Bak L K, Waagepetersen H S, Larsson O M: Role of astrocytic transport processes in glutamatergic and GABAergic neurotransmission. Neurocem Int, 45: 521-527, 2004.

Non Patent Literature 19: Huang Y H, Bergles D E: Glutamate transporters bring competition to the synapse. Curr Opin Neurobiol, 14: 346-352, 2004.

Non Patent Literature 20: Fellin T, Carmingnoto G: Neuron-to-astrocyte signaling in the brain represents a distinct multifunctional unit. J Physiol, 559: 3-15, 2004.

Non Patent Literature 21: Araque A, Perea G: Glial modulation of synaptic transmission in culture. Glia, 47: 241-248, 2004.

Non Patent Literature 22: Volterra A, Steinhauser C: Glial modulation of synaptic transmission in the hippocampus. Glia, 47: 249-257, 2004.

Non Patent Literature 23: Parpura V, Scemes E, Spray D C: Mechanisms of glutamate release from astrocytes: gap junction "hemichannels", purinergic receptors and exocytotic release. Neurochem Int, 45: 259-264, 2004.

Non Patent Literature 24: Bezzi P, Gundersen V, Galbete J L, Seifert G, Steinhauser C, et al.: Astrocytes contain a vesicular compartment that is competent for regulated exocytosis of glutamate. Nat Neurosci, 7: 613-620, 2004.

Non Patent Literature 25: Jahanshahi, M., Sadeghi, Y., Hosseini, A. et al.: The effect of spatial learning on the number of astrocytes in the CA3 subfield of the rat hippocampus. Singapore Med. J., 49, 388-391 (2008)

Non Patent Literature 26: Gibbs, M. E., O'Dowd, B. S., Hertz, E. et al.: Astrocytic energy metabolism consolidates memory in young chicks. Neuroscience, 141, 9-13 (2006)

Non Patent Literature 27: Cotter D R, Pariante C M, Everall I P: Glial cell abnormalities in major psychiatric disorders: The evidence and implications. Brain Res Bull, 55: 585-595, 2001.

Non Patent Literature 28: Nagai Kaoru (2005), Importance of Astrocyte in Neuropsychological Function, Yamanashi Medical Journal, 20, 25-31

Non Patent Literature 29: Yoshihisa Kudo, Shuichi Koizumi, Keiji Wada, and Kenji Hashimoto (2007) Production of pharmaceuticals which have glia cells as a target, Folia Pharmacologica *Japonica*, 130, 185-192.

Non Patent Literature 30: McCarth K D, de Vellis (1980) Preparation of separate astroglial and oligodendroglial cell cultures from rat cerebral tissue. J. Cell Biology, 85, 890-902.

Non Patent Literature 31: Nair J J, Aremu A O, van Staden J. (2011) Isolation of narciprimine from Cyrtanthus contractus (Amaryllidaceae) and evaluation of its acetylcholinesterase inhibitory activity. J. Ethnopharmacol. 137, 1102-1106.

Non Patent Literature 32: Sugimoto H, Yamanishi Y, limura Y, Kawakami Y. (2000) Donepezil hydrochloride (E2020) and other acetylcholinesterase inhibitors. Curr. Med. Chem. 7, 303-39.

Non Patent Literature 33: Yang P, Abe S, Sato Y, Yamashita T, Matsuda F, Hamayasu T, Imai K, Suzuki K. (2007) A palmitoyl conjugate of an insect pentapeptide causes growth arrest in mammalian cells and mimics the action of diapause hormone. J. Insect Biotech. Sericol. 79, 63-69.

Non Patent Literature 34: Asanuma M, Miyazaki I, Diaz-Corrales F J, Kimoto N, Kikkawa Y, Takeshima M, Miyoshi K, Murata M. (2010) Neuroprotective effects of zonisamide target astrocyte. Ann. Neurol. 67, 239-349.

Non Patent Literature 35: Bjornsen, L. P., Hadera, M. G., Zhou, Y., Danbolt, N. C., and Sonnewald, U. (2014) The GLT-1 (EAAT2; slc1a2) glutamate transporter is essential for glutamate homeostasis in the neocortex of the mouse. Journal of neurochemistry, 128 (5), 641-649.

Non Patent Literature 36: Toyomoto, M., Inoue, S., Ohta, K., Kuno, S., Ohta, M., Hayashi, K., and Ikeda, K. (2005). Production of NGF, BDNF and GDNF in mouse astrocyte cultures is strongly enhanced by a cerebral vasodilator, ifenprodil. Neuroscience letters, 379 (3), 185-189.

Non Patent Literature 37: Thakker-Varia, S., and Alder, J. (2009) Neuropeptides in depression: role of VGF. Behavioural brain research, 197 (2), 262-278.

Non Patent Literature 38: Tsushima, M., Yamamoto, K. I., Goryo, M., Suzuki, F., and Suzuki, K. (2010) Hot-water extract of *Paecilomyces tenuipes* from the silkworm pupae improves D-galactose-induced brain aging in mice. Journal of insect biotechnology and sericology, 79 (2), 45-51.

Non Patent Literature 39: Wang, D. D., and Bordey, A. (2008) The astrocyte odyssey. Progress in neurobiology, 86 (4), 342-367.

Non Patent Literature 40: Xu, P., Uchidate, M., Iwabuchi, A., Kondo, H., Matsui, Y., Mangetsu, M., and Suzuki, K. (2013) Mulberry twig extract counters hair aging in senescence-accelerated mice. Journal of Traditional Medicines, 30 (5), 229-235.

INDUSTRIAL APPLICABILITY

A novel cyclic peptide derivative which is useful in terms of having a physiological activity including an excellent astrocyte proliferative activity can be provided. In addition, with regard to the method for preparing it, it is possible to use as a raw material *Paecilomyces tenuipes* which is excellent in terms of cost and stable supply due to easy obtainability.

The invention claimed is:

1. A method of increasing expression of NGF and/or VGF by administering to a subject in need thereof a therapeutically effective amount of a cyclic peptide derivative represented by the following general formula (1)

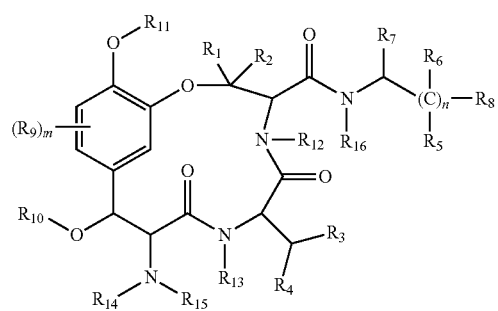
(1)

in the formula, m is 0 to 3, n≥1, $R_1$ to $R_6$ are independently a hydrogen atom or a hydrocarbon group, $R_7$ and $R_8$ are independently a carboxyl group or a salt thereof, or an alkoxycarbonyl group, $R_9$ is a hydrocarbon group, a hydroxyl group, an alkoxy group, or an alkylcarbonyloxy group, $R_{10}$ and $R_{11}$ are independently a hydrogen atom, a hydrocarbon group, or an alkylcarbonyloxy group, and $R_{12}$ to $R_{16}$ are independently a hydrogen atom or a hydrocarbon group.

2. A method of treating a brain disease by administering to a subject in need thereof a therapeutically effective amount of a cyclic peptide derivative represented by the following general formula (1)

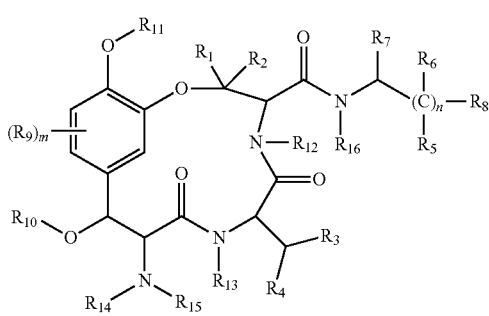
(1)

in the formula, m is 0 to 3, n≥1, $R_1$ to $R_6$ are independently a hydrogen atom or a hydrocarbon group, $R_7$ and $R_8$ are independently a carboxyl group or a salt thereof, or an alkoxycarbonyl group, $R_9$ is a hydrocarbon group, a hydroxyl group, an alkoxy group, or an alkylcarbonyloxy group, $R_{10}$ and $R_{11}$ are independently a hydrogen atom, a hydrocarbon group, or an alkylcarbonyloxy group, and $R_{12}$ to $R_{16}$ are independently a hydrogen atom or a hydrocarbon group; wherein the brain disease is one or more selected from the group consisting of Alzheimer's disease, Parkinson's disease, memory disorders, schizophrenia, bipolar disorder, and depression.

3. A method of improving hair quality by administering to a subject in need thereof a therapeutically effective amount of a cyclic peptide derivative represented by the following general formula (1)

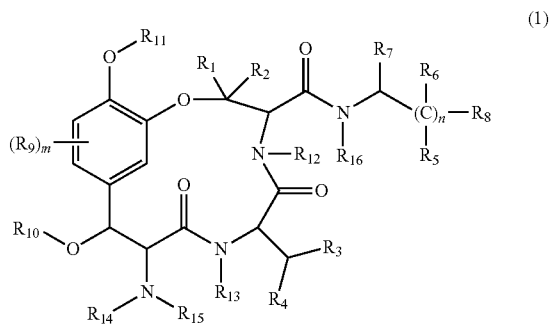
(1)

in the formula, m is 0 to 3, n≥1, $R_1$ to $R_6$ are independently a hydrogen atom or a hydrocarbon group, $R_7$ and $R_8$ are independently a carboxyl group or a salt thereof, or an alkoxycarbonyl group, $R_9$ is a hydrocarbon group, a hydroxyl group, an alkoxy group, or an alkylcarbonyloxy group, $R_{10}$ and $R_{11}$ are independently a hydrogen atom, a hydrocarbon group, or an alkylcarbonyloxy group, and $R_{12}$ to $R_{16}$ are independently a hydrogen atom or a hydrocarbon group.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: NGF forward primer

<400> SEQUENCE: 1
tgccaaggac gcagctttc                                                     19

<210> SEQ ID NO 2
<211> LENGTH: 25
<212> TYPE: DNA
<213> ORGANISM: Artificial Sequence
<220> FEATURE:
<223> OTHER INFORMATION: NGF reverse primer

<400> SEQUENCE: 2
tgaagtttag tccagtgggc ttcag                                              25

<210> SEQ ID NO 3
<211> LENGTH: 20
<212> TYPE: DNA
<213> ORGANISM: Artificial Sequence
<220> FEATURE:
<223> OTHER INFORMATION: GDNF forward primer

<400> SEQUENCE: 3
tcagctgccc agcacatttc                                                    20

<210> SEQ ID NO 4
<211> LENGTH: 22
<212> TYPE: DNA
<213> ORGANISM: Artificial Sequence
<220> FEATURE:
<223> OTHER INFORMATION: GDNF reverse primer

<400> SEQUENCE: 4
tgggagcatc agctaccaca tc                                                 22

<210> SEQ ID NO 5
<211> LENGTH: 24
<212> TYPE: DNA
<213> ORGANISM: Artificial Sequence
<220> FEATURE:
<223> OTHER INFORMATION: VEGF-A forward primer

<400> SEQUENCE: 5
acattggctc acttccagaa acac                                               24
```

<210> SEQ ID NO 6
<211> LENGTH: 21
<212> TYPE: DNA
<213> ORGANISM: Artificial Sequence
<220> FEATURE:
<223> OTHER INFORMATION: VEGF-A reverse primer

<400> SEQUENCE: 6
tggttggaac cggcatcttt a                                              21

<210> SEQ ID NO 7
<211> LENGTH: 25
<212> TYPE: DNA
<213> ORGANISM: Artificial Sequence
<220> FEATURE:
<223> OTHER INFORMATION: BDNF forward primer

<400> SEQUENCE: 7
gccgtttacc aaattaacct ttgtc                                          25

<210> SEQ ID NO 8
<211> LENGTH: 22
<212> TYPE: DNA
<213> ORGANISM: Artificial Sequence
<220> FEATURE:
<223> OTHER INFORMATION: BDNF reverse primer

<400> SEQUENCE: 8
ccacacaatt gctgatgtct cc                                             22

<210> SEQ ID NO 9
<211> LENGTH: 23
<212> TYPE: DNA
<213> ORGANISM: Artificial Sequence
<220> FEATURE:
<223> OTHER INFORMATION: VGF forward primer

<400> SEQUENCE: 9
ccagacggga aaggctgttc tat                                            23

<210> SEQ ID NO 10
<211> LENGTH: 25
<212> TYPE: DNA
<213> ORGANISM: Artificial Sequence
<220> FEATURE:
<223> OTHER INFORMATION: VGF reverse primer

<400> SEQUENCE: 10
ggagaagtgg gtaagttcac agcaa                                          25

<210> SEQ ID NO 11
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 11
gtctcctctg acttcaaca                                                 19

<210> SEQ ID NO 12
<211> LENGTH: 20
<212> TYPE: DNA
<213> ORGANISM: Artificial Sequence
<220> FEATURE:

```
<223> OTHER INFORMATION: GAPDH reverse primer

<400> SEQUENCE: 12
caggaaatga gcttgacaaa                                                    20
```